United States Patent
Asghari et al.

(10) Patent No.: US 10,745,454 B2
(45) Date of Patent: Aug. 18, 2020

(54) METHOD OF SYNTHESIZING ANTAGONIST PEPTIDES FOR CELL GROWTH

(71) Applicants: Seyed Mohsen Asghari, Dubai (AE); Somayeh Ehtesham, Dubai (AE)

(72) Inventors: Seyed Mohsen Asghari, Dubai (AE); Somayeh Ehtesham, Dubai (AE)

(*) Notice: Subject to any disclaimer, the term of this patent is extended or adjusted under 35 U.S.C. 154(b) by 0 days.

(21) Appl. No.: 16/042,284

(22) Filed: Jul. 23, 2018

(65) Prior Publication Data
US 2019/0233490 A1    Aug. 1, 2019

Related U.S. Application Data

(60) Provisional application No. 62/624,505, filed on Jan. 31, 2018.

(51) Int. Cl.
| | | |
|---|---|---|
| A61K 38/08 | (2019.01) | |
| A61K 38/10 | (2006.01) | |
| C07K 7/06 | (2006.01) | |
| C07K 7/08 | (2006.01) | |
| C07K 14/49 | (2006.01) | |
| G01N 33/50 | (2006.01) | |
| C07K 14/50 | (2006.01) | |
| G01N 33/68 | (2006.01) | |

(52) U.S. Cl.
CPC ............. *C07K 14/49* (2013.01); *C07K 7/06* (2013.01); *C07K 7/08* (2013.01); *C07K 14/503* (2013.01); *G01N 33/5011* (2013.01); *G01N 33/6872* (2013.01); *A61K 38/08* (2013.01); *A61K 38/10* (2013.01); *G01N 2333/503* (2013.01); *G01N 2333/52* (2013.01)

(58) Field of Classification Search
CPC .......... A61K 38/08; A61K 38/18; C07K 7/06; C07K 14/475; C07K 14/503
See application file for complete search history.

(56) References Cited

U.S. PATENT DOCUMENTS 5,840,693 A * 11/1998 Eriksson ............... C07K 14/52
514/8.1
2018/0231563 A1* 8/2018 Shimada ............... G01N 27/62

* cited by examiner

*Primary Examiner* — Jeffrey E. Russel
(74) *Attorney, Agent, or Firm* — Barry Choobin; Patent 360

(57) ABSTRACT

The embodiments herein disclose a method for synthesizing antagonistic peptide VEGF and bFGF. The method comprises synthesizing the antagonistic peptide for VEGF and bFGF and analyzing the purity of peptides. The quality of antagonistic peptide for VEGF and bFGF is analyzed by HPLC chromatogram and Mass spectrometry analysis. The biochemical activity of the antagonistic peptide for VEGF and bFGF is analyzed by competitive binding assay, cell proliferation assay, Matrigel assay for anti-angiogenic activity analysis, histopathological staining and Western blot analysis. The competitive binding assay of antagonistic peptide for VEGF and bFGF illustrate that peptides binds with cell receptors at a concentration of 2000 ng/ml. The cell proliferation assay illustrates that cell growth is arrested when antagonistic peptide for VEGF and bFGF are at a concentration of 2000 ng/ml. The anti-angiogenic activity analysis illustrates that angiogenesis is arrested when the concentration of antagonistic peptide for VEGF and bFGF is 2000 ng/ml.

10 Claims, 15 Drawing Sheets
Specification includes a Sequence Listing.

SEQUENCE LISTING

```
<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Cys Gln Val Leu Ile Ser Gln Leu Cys
1               5

<210> SEQ ID NO 2
<211> LENGTH: 10
<212> TYPE: PRT
<213> ORGANISM: Homo sapiens

<400> SEQUENCE: 2

Cys Pro Asp Asp Gly Leu Glu Cys Val Pro
1               5                   10

<210> SEQ ID NO 3
<211> LENGTH: 5
<212> TYPE: PRT
<213> ORGANISM: Homo sapiens

<400> SEQUENCE: 3
```

```
Cys Glu Cys Arg Pro
1               5

<210> SEQ ID NO 4
<211> LENGTH: 18
<212> TYPE: PRT
<213> ORGANISM: Homo sapiens

<400> SEQUENCE: 4

Asp Ile Phe Gln Glu Tyr Pro Asp Glu Ile Glu Tyr Ile Phe Lys Pro
1               5                   10                  15

Ser Cys

<210> SEQ ID NO 5
<211> LENGTH: 9
<212> TYPE: PRT
<213> ORGANISM: Homo sapiens

<400> SEQUENCE: 5

Leu Lys Arg Thr Gly Gln Tyr Lys Leu
1               5

<210> SEQ ID NO 6
<211> LENGTH: 11
<212> TYPE: PRT
<213> ORGANISM: Homo sapiens

<400> SEQUENCE: 6

Cys Leu Lys Arg Thr Gly Gln Tyr Lys Leu Cys
1               5                   10
```

METHOD OF SYNTHESIZING ANTAGONIST PEPTIDES FOR CELL GROWTH

SEQUENCE LISTING

I hereby state that the amendments were made in accordance with 37 CFR 1.825 (a), included in the ASC II file submitted electronically. The ASC II file was created on Feb. 25, 2019, named W 7134834.txt and is 19.5 KB in size. The ASC II file resubmitted on May 31, 2019 incorporates all the sequences disclosed earlier and included as reference herein. I hereby state that the sequence listing submitted does not comprise new matter.

BACKGROUND

Technical Field

The embodiments herein generally relate to the field of cell growth. The embodiments herein particularly relate to antagonists of vascular endothelial growth factor (VEGF) and fibroblast growth factor (FGF) used for diagnosis and prognosis of cancer. The embodiments herein more particularly relate to a method of synthesizing antagonist peptide used for therapeutic applications of VEGF and FGF in cancer treatment.

Description of the Related Art

Cancer is one of the most deadly threats to human health. In U.S alone, cancer affects nearly 1.3 million new patients each year and is the second leading cause of death after cardiovascular disease, accounting for approximately 1 in 4 deaths. Solid tumors are responsible for most of the deaths. Although there have been significant advances in the medical treatment of certain cancers, the overall 5-year survival rate for all cancer has improved only by about 10% in the past 20 years. Cancer or malignant tumors metastasizes and grow rapidly in an uncontrolled manner thereby making a timely detection and treatment of cancers extremely difficult.

The currently available methods of treating cancer are relatively non selective and generally target the tumor after the cancer has progressed to a more malignant stage. Surgery is carried out to remove the diseased tissue, the radiotherapy treatment is performed to shrink the solid tumors and chemotherapy is used to kill a rapidly diving cells. Chemotherapy treatment, in particular, results in numerous side effects. In some cases, the damage is so severe that the dosage given has to be limited and the use of potentially effective drugs is precluded. Moreover, cancer cells often develop resistance to chemotherapeutic drugs. The treatment of benign tumors at early stage is desired for preventing progression to a malignant or metastatic state, thereby reducing the morbidity and mortality or metastatic associated with cancer.

Angiogenesis is an important cellular event, in which vascular endothelial cells proliferate, prune and reorganize to form new vessels from pre-existing vascular network. There is a compelling evidence to indicate or stress the fact that the development of a vascular supply is essential for normal and pathological cell proliferative processes. A delivery of oxygen and nutrients in addition to the removal of catabolic products, represent rate-limiting steps in the majority of growth processes occurring in multicellular organisms.

While induction of new blood vessels is considered to be a predominant mode of tumor angiogenesis, a plurality of recent studies have indicated that some tumors is found to grow by co-opting the existing host blood vessels. The co-opted vascular then regresses, leading to tumor regression that is eventually reversed by hypoxia induced angiogenesis at the tumor margin.

Growth factors are proteins that function as growth stimulators (mitogens) and/or growth inhibitors, configured to stimulate cell mitigation, act as chemotactic agents, modulate differentiated function of cells, involved in apoptosis, involved in angiogenesis and promote survival of cells without influencing growth and differentiation.

One of the key positive regulators of both normal and abnormal angiogenesis is vascular endothelial growth factor (VEGF-A). VEGF-A is a part of a gene family comprising VEGF-B, VEGF-C, VEGF-C, VEGF-D, VEGF-E, VEGF-F and PIGF. VEGF-A primarily binds to two high affinity receptor tyrosine kinase. Among VEGFR-1 (Flt-1) and VEGFR-2 (Flk-1/KDR), the latter is the major transmitter of vascular endothelial cell mitogenic signals of VEGF-A. Additionally neuropilin-I has been identified as a receptor for heparin binding VEGF-A isoforms and plays an important role in vascular development.

Vascular endothelial cells (VEGF) comprises of five glycoproteins VEGF-A, VEGF-B, VEGF-C, VEGF-D and Placenta growth factor (PIGF), which regulate both vasculogenesis and angiogenesis. In addition, alternative exon splicing generates four VEGF isoforms. The VEGF family members bind to at least one of the three known vascular endothelial growth factor receptors (VEGFRs) namely VEGFR-1 (FLT-1), VEGFR-2 (FLK-1 or KDR) and VEGFR-3 (FLT-4). VEGFA binds to VEGFR-1 and VEGFR-2, whereas VEGFB and PIGF have high affinity towards VEGFR-1 for binding. Unlike VEGFR-3 which is largely restricted to lymphatic endothelial cells, both VEGFR-1 and VEGFR-2 are expressed in vascular endothelial cells, as well as monocytes, macrophages (VEGFR-1), and hematopoietic stein cells (VEGFR-2). Importantly, expression of VEGFR-1 and VEGFR-2 as well as the co-receptors NP1 and NP2, has been detected on subsets of solid tumor cells and activation of VEGFR-1 in breast cancer cells which supports the cancel cell growth and survival.

The fibroblast growth factor (FGF) signaling network plays a ubiquitous role in normal cell growth, survival, differentiation and angiogenesis, but has also been implicated in tumor development. Fibroblast growth factors (FGFs) are widely expressed in both developing and adult tissues and play important roles in a variety or normal and pathological processes, including tissue development, tissue regeneration, angiogenesis, and neoplastic transformation. In humans 22 members of the FGF family have been identified. In contrast to their ligands, only four human FGFRs exist, designated FGFR-1 to FGFR-4. FGF signaling pathways have been implicated in tumor development and progression. The effects of increased FGF receptor signaling are wide ranging, involving both tumor cells and the surrounding stroma, including the vasculature, and this dual activity plays an important role in tumorigenesis. The potential of FGFs to promote tumor progression is highly dependent on specific FGFR signaling. FGF-1 (acidic FGF) and FGF-2 (basic FGF), and their receptors promote autocrine and paracrine growth control of malignant tumors, while the FGF-2 ligand has been shown to have potent angiogenesis activity. FGFs have been illustrated to increase the motility and invasiveness of a variety of cancers, the FGF signaling network thus makes an attractive anti-neoplastic target across a range of tumor types.

Vascular endothelial growth factor (VEGF) isoforms and fibroblast growth factors (FGFs) are amongst the growth factors that are directly associated with large number of cancers expressing VEGFR-1 (known as FLT-1) and/or VEGFR-2 (known as KDR) and bFGFR. The inhibition of VEGF of bFGF binding to the respective receptor is applied for treatment of a plurality of cancers.

In addition to being an angiogenic factor, VEGF as a pleiotropic growth factor, exhibits multiple biological effects in other physiological processes, such as endothelial cell survival and proliferation, vessel permeability and vasodilation, monocyte chemotaxin and calcium influx. The earlier prior arts report mitogenic on a few non-endothelial cell types such as retinal pigment, epithelial cells, pancreatic duct cells and Schwann cells.

The recognition of VEGF as a primary regulator of angiogenesis in pathological conditions has led to numerous attempts.

Interactions between polypeptide ligands and their cognate receptor are critical for a variety of biological process including maintenance of cellular and organism homeostasis, cellular development and tumorigenesis. The cell signaling network created by these ligands and receptor interactions is responsible for relaying a majority of the extracellular, intracellular and intracellular signals handing off signals from one member of the pathway to the next. Modulation of one member of the pathway can be relayed through the signal transduction pathway, resulting in modulation of activities of other pathway members and modulating outcomes of such signals transduction such as affecting phenotypes and responses of a cell or organism to a signal. Diseases and disorders can and often do involve deregulated signal transduction pathways. Many ligands can activate multiple independent pathways and the strength of the activation of different pathways can be modulated by the presence or absence of signals generated by other ligands or receptors.

For example, epidermal growth factor (EGF) is a 53 amino acid cytokine which plays an important role in the growth control of mammalian cells. It is proteolytically cleaved from a large integral membrane protein precursor. Human Epidermal Receptor (HER), including epidermal growth factor receptor (EGFR) is well known examples of receptors tyrosine kinase.

Interaction of HERs with their cognate ligands or with structurally related ligands leads to dimerization and activation of the kinase domain. This initiates a signaling cascade, leading to cell division, dysregulation of HER signaling such as the over expression of the genes coding for HER family members has been implicated in a number of pathologies, especially cancers of the breast ovary head and neck.

Although these therapeutics have been illustrating to be effective in some cases, there is still a need for novel therapies for HER-related pathologies particularly therapeutics compounds which interfere with the entire receptor family in a panoramic fashion.

Current methods of synthesis and expression of polypeptides provide a backdrop for the discovery, investigation and validation of new methods of designing optimized ligands or receptor having panoramic therapeutic properties. These optimized molecules can then be exploited in the area of drug discovery and medicine including gene therapy.

Hence there is a need for identifying the portions of vascular endothelial growth factor (VEGF) and fibroblast growth factor (FGF) peptides which act as antagonist of VEGF-A, VEGF-B and bFGF respectively. Also, there is a need for peptide antagonists of VEGF-A, VEGF-B and bFGF for treating the physiological conditions associated with angiogenesis and neovascularization. Further there is a need to use the peptide antagonists of VEGF-A, VEGF-B and bFGF for diagnosis of disease or condition which occur with over expression of VEGF and/or bFGF receptors. These peptide antagonists of VEGF-A, VEGF-B and bFGF are tools for analyzing the cellular pathways which depend on the activation of VEGF and/or bFGF receptors.

The above-mentioned shortcomings, disadvantages and problems are addressed herein and which will be understood by reading and studying the following specification

OBJECTIVES OF THE EMBODIMENTS

The primary objective of the embodiment herein is to identifying the portions of vascular endothelial growth factor (VEGF) and fibroblast growth factor (FGF) which act as antagonist of VEGF-A, VEGF-B and/or bFGF respectively.

Another object of the embodiment herein is to provide peptide antagonists of VEGF-A, VEGF-B and bFGF for treating the physiological conditions associated with angiogenesis and neovascularization.

Yet another object of the embodiment herein is to provide peptide antagonists of VEGF-A, VEGF-B and/or bFGF for diagnosis of disease or condition which occur with over expression of VEGF and/or bFGF receptors.

Yet another object of the embodiment herein is to provide a peptide antagonist of VEGF-A, VEGF-B and bFGF are tools for analyzing the cellular pathways which depend on the activation of VEGF and/or bFGF receptors.

Yet another object of the embodiment herein is to provide peptide antagonists of VEGF-A, VEGF-B and bFGF in the form of fusion protein or conjugated protein to a moiety to enhance purification, increase stability and/or to provide a biological activity.

Yet another object of the embodiment herein is to provide peptide antagonists of VEGF-A, VEGF-B and/or bFGF as carrier for delivering therapeutic agents to cells expressing VEGFR-1/-2 or bFGFR-1/-2.

Yet another object of the embodiment herein is to provide peptide antagonists of VEGF-A, VEGF-B and/or bFGF which simultaneously block both the VEGFR-1, VEGFR-2 and/or bFGFR1.

These objects and the other advantages of the embodiments herein will become readily apparent from the following detailed description taken in conjunction with the accompanying drawings.

SUMMARY

The various embodiments herein identify the portions of vascular endothelial growth factor (VEGF) and fibroblast growth factor (FGF) which act as antagonist of VEGF-A, VEGF-B and bFGF respectively. The embodiments herein provide growth factor antagonist peptides of VEGF-A, VEGF-B and bFGF for treating the physiological conditions associated with angiogenesis and neovascularization. The embodiments herein provide peptide antagonists of VEGF-A, VEGF-B and bFGF for diagnosis of disease or condition which occur with over expression of VEGF and/or bFGF receptors.

According to one embodiment herein, a method for synthesizing antagonistic peptide for vascular endothelial growth factor (VEGF) and basic fibroblast growth factor (bFGF), comprises the following steps. The antagonistic peptide for vascular endothelial growth factor (VEGF) and basic fibroblast growth factor (bFGF) are synthesized by a protocol. The purity of the antagonistic peptide for vascular endothelial growth factor (VEGF) and basic fibroblast growth factor (bFGF) is analyzed by a protocol. A plurality of physico-chemical qualities of the antagonistic peptide for vascular endothelial growth factor (VEGF) and basic fibroblast growth factor (bFGF) are analyzed by a plurality of methods. The plurality of methods are HPLC chromatogram and Mass spectrometry analysis. The cyclization of peptides in the antagonistic vascular endothelial growth factor (VEGF) peptide and basic fibroblast growth factor (bFGF) peptide is analyzed by a protocol. The disulfide bond formation in the antagonistic peptide for vascular endothelial growth factor (VEGF) and basic fibroblast growth factor (bFGF) is analyzed by a protocol. The synthesized antagonistic peptide for vascular endothelial growth factor (VEGF) and basic fibroblast growth factor (bFGF) are annotated as Seq. ID No. 1 peptide, Seq. ID No. 2 peptide, Seq. ID No. 3 peptide, Seq. ID No. 4 peptide and Seq. ID No. 5 peptide. The Seq. ID No. 1 peptide, Seq. ID No. 2 peptide, Seq. ID No. 3 peptide are antagonists of both VEGF-A and VEGF-B. The Seq. ID No. 1 peptide, Seq. ID No. 2 peptide, Seq. ID No. 3 peptide in combination acts as antagonist for both VEGF-A and VEGF-B. The Seq. ID No. 4 peptide is antagonist of VEGF-A. The Seq. ID No. 5 peptide is antagonist of bFGF. The biochemical activity of the antagonistic peptide for vascular endothelial growth factor (VEGF) and basic fibroblast growth factor (bFGF) is analyzed by competitive binding assay, cell proliferation assay, Matrigel assay for anti-angiogenic activity analysis, histopathological staining and Western blot analysis.

According to one embodiment herein, the Seq. ID No. 1 peptide comprises a biochemical structure represented by 2HN-Cys-Gln-Val-Leu-Ile-Ser-Gln-Leu-Cys-COOH. The Seq. ID No. 1 comprises seven amino acid residues derived from VEGF-B (Gln46, Val48, Leu81, Ile83, Ser88, Gln89 and Leu90). The Seq. ID No. 1 comprises two Cys residues for chain cyclization. The Seq. ID No. 1 peptide binds and blocks vascular endothelial growth factor receptor-1 and vascular endothelial growth factor receptor-2 (VEGFR-1 and VEGFR-2).

According to one embodiment herein, the Seq. ID No. 2 peptide comprises amino acid residues derived from VEGF-B. The Seq. ID No. 2 comprises of amino acid residues 61-70 in VEGF-B. The Seq. ID No. 2 comprises a biochemical structure represented by 2HN-Cys61-Pro62-Asp63-Asp64-Gly65-Leu66-Glu67-Cys68-Val69-Pro70-COOH. The Seq. ID No. 2 peptide binds and blocks vascular endothelial growth factor receptor-1 and vascular endothelial growth factor receptor-2 (VEGFR-1 and VEGFR-2).

According to one embodiment herein, the Seq. ID No. 3 peptide comprises amino acid residues derived from VEGF-B. The Seq. ID No. 3 comprises of amino acid residues 101-105 in VEGF-B. The Seq. ID No. 3 comprises a biochemical structure represented by 2HN-Cys101-Glu102-Cys103-Arg104-Pro105-COOH. The Seq. ID No. 3 peptide binds and blocks vascular endothelial growth factor receptor-1 and vascular endothelial growth factor receptor-2 (VEGFR-1 and VEGFR-2).

According to one embodiment herein, the Seq. ID No. 4 peptide comprises amino acid residues derived from VEGF-A. The Seq. ID No. 4 comprises of amino acid residues 34-51 in VEGF-A. The Seq. ID No. 4 comprises a biochemical structure represented by 2HN-Asp34-Ile35-Phe36-Gln37-Glu38-Tyr39-Pro40-Asp41-Glu42-Ile43-Glu44-Tyr45-Ile46-Phe47-Lys48-Pro49-Ser50-Cys51-COOH. The cysteine residue is added optionally to the N-terminus of Seq. ID No. 4 for chain cyclization. The Seq. ID No. 4 peptide binds and blocks vascular endothelial growth factor receptor 2 (VEGFR-2).

According to one embodiment herein, Seq. ID No. 1 peptide, Seq. ID No. 2 peptide, Seq. ID No. 3 peptide and Seq. ID No. 4 peptide bind and block vascular endothelial growth factor receptors 1 (VEGFR-1) and/or vascular endothelial growth factor receptors 2 (VEGFR-2). The predetermined combination of Seq. ID No. 1 peptide, Seq. ID No. 2 peptide, Seq. ID No. 3 peptide and Seq. ID No. 4 peptides or their fragments comprising a disulfide bond bind and block vascular endothelial growth factor receptors 1 (VEGFR-1) and/or vascular endothelial growth factor receptors 2 (VEGFR-2).

According to one embodiment herein, the Seq. ID No. 5 peptide comprises amino acid residues derived from bFGF. The Seq. ID No. 5 comprises a biochemical structure represented by 2HN-Leu119-Lys120-Arg121-Thr122-Gly123-Gln124-Tyr125-Lys126-Leu127-COOH. A plurality of cysteine residues are added optionally to the N-terminus and C-terminus of Seq. ID No. 5 for chain cyclization. Cysteine residues are added to the N-terminus and C-terminus of Seq. ID No. 5 to obtain a biochemical structure represented by 2HN-Cys-Leu-Lys-Arg-Thr-Gly-Gln-Tyr-Lys-Leu-Cys-COOH (Seq. ID No. 6). The Seq. ID No. 5 peptide binds and blocks basic fibroblast growth factor-receptors 1 (bFGFR-1). The Seq. ID No. 5 peptide binds and blocks vascular endothelial growth factor receptor 1 (VEGFR-1) and/or vascular endothelial growth factor receptor 2 (VEGFR-2) and basic fibroblast growth factor-receptor 1 (bFGFR-1) with a predetermined combination of Seq. ID No. 6 peptide and with at least one of Seq. ID No. 1 to Seq. ID No. 4.

According to one embodiment herein, antagonistic peptide for vascular endothelial growth factor (VEGF) and basic fibroblast growth factor (bFGF) comprises amino-acids residues in a range of 5 to 54 amino acids or a segment thereof. The antagonistic peptide for vascular endothelial growth factor (VEGF) and basic fibroblast growth factor (bFGF) binds and blocks vascular endothelial growth factor receptors 1 and/or 2 (VEGFR-1 and VEGFR2) and/or basic fibroblast growth factor-receptors 1 and/or 2 (bFGFR-1 and bFGFR-2). The antagonistic peptide for vascular endothelial growth factor (VEGF) and basic fibroblast growth factor (bFGF) Seq. ID No. 1-Seq. ID No. 5 are with or without an additional disulfide bond. The antagonistic peptide for vascular endothelial growth factor (VEGF) and basic fibroblast growth factor (bFGF) Seq. ID No. 1-Seq. ID No. 5 peptides comprises a plurality of diagnostic, therapeutic and theranostic properties. The plurality of diagnostic, therapeutic and theranostic properties of Seq. ID No. 1-Seq. ID No. 5 peptides is induced by a plurality of amino acid substitutions and a plurality of different amino acid positions.

According to one embodiment herein, a plurality of diagnostic, therapeutic and theranostic properties of Seq. ID No. 1-Seq. ID No. 5 peptides is observed in VEGF and bFGF antagonistic sequences comprising a sequence similarity of more than 70% with a parent peptide sequence. The diagnostic, therapeutic and theranostic properties of Seq. ID No. 1-Seq. ID No. 5 peptides is observed in VEGF and bFGF antagonistic sequences along with a pharmaceutically acceptable carrier. The Seq. ID No. 1-Seq. ID No. 5 peptides are linked to a heterologous peptide and/or protein. The theranostic property is also used for topically administrating a plurality of therapeutic compositions. The plurality of therapeutic compositions comprises cream, lotion, solution and lip balm.

According to one embodiment herein, the Seq. ID No. 1-Seq. ID No. 5 peptides illustrate anti-angiogenesis activity. The Seq. ID No. 1-Seq. ID No. 5 peptides are useful for treatment of an angiogenesis-related disease. The angiogenesis-related disease are selected from the group consisting of cancer, ascites formation, psoriasis, age-related macular degeneration, thyroid hyperplasia, preeclampsia, rheumatoid arthritis and osteoarthritis, Alzheimer's disease, obesity, pleura effusion, atherosclerosis, endometriosis, diabetic/other retinopathies, neovascular glaucoma, age-related macular degeneration, hemangiomas, and corneal neovascularization.

According to one embodiment herein, the competitive binding assay of antagonistic peptide for vascular endothelial growth factor (VEGF) and basic fibroblast growth factor (bFGF) binds with the cell receptors at a concentration of 2000 ng/ml. The cell proliferation assay illustrates that the cell growth is arrested when the antagonistic peptide for vascular endothelial growth factor (VEGF) and basic fibroblast growth factor (bFGF) are at a concentration of 2000 ng/ml. The anti-angiogenic activity result analysis illustrates that the angiogenesis in the cells is arrested when the concentration of antagonistic peptide for vascular endothelial growth factor (VEGF) and basic fibroblast growth factor (bFGF) is 2000 ng/ml.

According to one embodiment herein, portions of VEGF-A or VEGF-B which act as antagonists of VEGF-A and/or VEGF-B binding to VEGFR-1 and/or VEGFR-2 (seq.ID No 1 to 4) are identified. A portion of bFGF which acts as antagonist of bFGF binding to bFGF receptor is also identified. The peptides are antagonists against the major isoforms of VEGF and bFGF. The peptides are used alone or in combination, to treat diseases and conditions associated with VEGF- and/or bFGF-induced neovascularization or angiogenesis.

According to one embodiment herein, the peptides include any of Seq. ID NO.1 to 4 comprising vascular endothelial growth factor (VEGF) antagonist activity. The VEGF antagonist activity is illustrated/determined by the human umbilical vein endothelial cell (HUVEC) proliferation, angiogenesis and stimulation by VEGF-A.

According to one embodiment herein, the peptides comprising Seq. ID NO.5 or a portion thereof having bFGF antagonist activity. The bFGF antagonist activity is determined by the human umbilical vein endothelial cell (HUVEC) proliferation, angiogenesis and stimulation by bFGF.

According to one embodiment herein, the peptides of Seq. ID NO 1 comprise analogs. The "analogs" refers to a peptide differing from the sequence of one of the peptides of the parent peptide molecule (VEGF) but which still exhibits VEGF antagonist activity. The analog or antagonist peptide molecule has 50% of the VEGF antagonist activity of the peptide of SEQ ID NO: 1 to 4. The antagonist activity of the analog is analyzed in the human umbilical vein endothelial cell (HUVEC) proliferation assay using VEGF-A, or peptide of SEQ ID NO: 5 in the human umbilical vein endothelial cell (HUVEC) proliferation assay using bFGF.

According to one embodiment herein, the analog or antagonist peptides exhibits 75% of the VEGF antagonist activity of the peptide of SEQ ID NO: 1 to 4, or the bFGF antagonist activity of the peptide of SEQ ID NO: 5.

According to one embodiment herein, the differences are preferably conservative amino acid substitutions, in which an amino acid is replaced with another naturally occurring amino acid of similar character. For example, the following substitutions are considered "conservative": Gly⇌Ala; Val⇌Leu⇌Met; Asp⇌Glu; Lys⇌Arg; Asn⇌Gln; and Phe⇌Trp⇌Tyr; Ser⇌Thr. Non-conservative changes are generally substitutions of one of the above amino acids with an amino acid from a different group (e.g., substituting Asn for Glu), or substituting Cys, Met, His, or Pro for any of the above amino acids.

According to one embodiment herein, the growth factor antagonistic peptides are part of a fusion protein or conjugated to a moiety to enhance purification, increase stability and/or to provide a biological activity.

According to one embodiment herein, the growth factor antagonistic peptides either alone, or as part of a fusion protein, are used to target cells expressing the VEGFR-1/-2 or bFGFR-1/-2 (receptors). The receptor targeting is used for diagnostic as well as therapeutic applications. For example, for diagnostic purposes the polypeptide is radio labeled and used to detect cells expressing the VEGFR-1/-2 or bFGFR-1/-2. It is found that expression of these receptors has a high correlation to disease state in a number of cancers, such as prostate and breast, particularly metastatic cancers. Accordingly, these peptides can be used in a prognostic manner for particular cancers.

According to one embodiment herein, for therapeutic applications, the growth factor antagonistic peptides are used to deliver therapeutic agents to cells expressing the VEGFR-1/-2 or bFGFR-1/-2 (receptors). For example, the peptides are used as carriers to deliver a desired chemical or cytotoxic moiety to the cells. The cytotoxic moiety may be a cytotoxic drug or an enzymatically active toxin of bacterial, fungal or plant origin, an enzymatically active polypeptide chain or fragment ("A chain") of such a toxin. The enzymatically active toxins and fragments thereof are preferred and are exemplified by diphtheria toxin A fragment, non-binding active fragments of diphtheria toxin, exotoxin A (from *Pseudomonas aeruginosa*), ricin A chain, abrin A chain, modeccin A chain, alphasarcin, certain *Aleurites fordii* proteins, certain Dianthin proteins, *Phytolacca americana* proteins (PAP, PAPII and PAP-S), *Momordica charantia* inhibitor, curcin, crotin, *Saponaria officinalis* inhibitor, gelonin, mitogellin, restrictocin, phenomycin, and enomycin. Ricin A chain, *Pseudomonas aeruginosa* exotoxin A and PAP are preferred.

According to one embodiment herein, the growth factor antagonistic peptides are used for the treatment of a disease or a plurality of disorder/condition associated with vascular endothelial growth factor (VEGF)-induced neovascularization or angiogenesis [the term "neovascularization" refers to the growth of blood vessels and capillaries] includes, but are not limited to retinal neovascularization, hemangiomas, solid tumor growth, leukemia, metastasis, psoriasis, neovascular glaucoma, diabetic retinopathy, rheumatoid arthritis, osteoarthritis, endometriosis, muscular degeneration and retinopathy of prematurity (ROP).

According to one embodiment herein, the growth factor antagonistic peptides of VEGF or bFGF which are capable of inhibiting, sequestering, or neutralizing one or more of the biological activities of VEGF and/or FGF are provided. The peptide antagonists of VEGF or bFGF act by interfering with the binding of VEGF and/or bFGF to a cellular receptor thereby incapacitating or killing cells which have been activated by VEGF or FGF, or by interfering with vascular endothelial cell activation after VEGF or bFGF binding to a cellular receptor. The specific binding is used for diagnosis of cells having the respective receptor(s) on their surface.

According to one embodiment herein, the growth factor antagonistic peptides of VEGF-A and/or VEGF-B are classified based on families of peptide antagonists. The first family comprises of amino acid residues that make a sequence different from that of VEGF-B but located in the vicinity of each other in the 3D structure (Seq. ID No: 1), and the second family is based upon three fragments from the VEGF-B or VEGF-A (Seq ID. 2 to 4). The first family comprises a peptide with the sequence of 2HN-Cys-Gln-Val-Leu-Ile-Ser-Gln-Leu-Cys-COOH (Seq. ID No: 1). The Seq. ID No. 1 comprises seven residues derived from VEGF-B including Gln46, Val48, Leu81, Ile83, Ser88, Gln89 and Leu90, and two cysteine residues for chain cyclization. The second family comprises amino acid residues appearing at positions 61-70 of VEGF-B including 2HN-Cys61-Pro62-Asp63-Asp64-Gly65-Leu66-Glu67-Cys68-Val69-Pro70-COOH (Seq. ID No. 2) and/or 101-105 of VEGF-B including 2HN-Cys101-Glu102-Cys103-Arg104-Pro105-COOH (Seq. ID No. 3), and/or 34-51 of VEGF-A including 2HN-Asp34-Ile35-Phe36-Gln37-Glu38-Tyr39-Pro40-Asp41-Glu42-Ile43-Glu44-Tyr45-Ile46-Phe47-Lys48-Pro49-Ser50-Cys51-COOH and a cysteine residue in the N-terminus for chain cyclization (Seq. ID No: 4). The Seq. ID No. 1 to 4 are combined in any order and amino acids residues are substituted in every position in their sequence with a similar residue. The Seq. ID No. 2 and 3 may comprise a disulfide bond. The antagonists of VEGF act alone or in combination by interfering with the binding of VEGF-A or VEGF-B to VEGF-receptor 1 (VEGF-R1) and/or VEGF-receptor 2 (VEGF-R2). The antagonists or antagonist peptides of receptors block cells which are activated by VEGF-A or VEGF-B.

According to one embodiment herein, antagonist of basic fibroblast growth factor (bFGF) is based upon a fragment from the native hormone bFGF including those residues at positions 119-127 of bFGF and two cysteine residues at N-terminal and C-terminal having the sequence of 2HN-Cys-Leu-Lys-Arg-Thr-Gly-Gln-Tyr-Lys-Leu-Cys-COOH (Seq. ID No. 6). Moreover, some substitutions are made in the sequence comprising substitutions of similar type of amino acids. The basis for the antagonistic action exhibited by these Seq. ID No. 5 peptides is an interaction with the bFGF-R1 (receptor), and consequently suppressing bFGF-induced proliferation of ovarian cancer cell line SKOV3. The SKOV3 cell line is known to highly express bFGFR-1, in cell culture. Further antagonists may lack one or more amino acids at the N-terminal or C-terminal of Seq. ID No. 5.

According to one embodiment herein, the term a "derivative" of a VEGF antagonist peptide or bFGF antagonist peptide is used to describe a peptide in which one or more physical, chemical, or biological properties has been altered. Such modifications comprise, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the peptide with other organic and non-organic molecules; and other modifications, any of which may result in changes in structure. These peptide derivatives exhibit at least one of the aforementioned antagonists' activities.

According to one embodiment herein, the function of the growth factor antagonistic peptides is analyzed by a plurality of standard methods/protocols. The activity of antagonist is determined using standard protocols/methods. The peptide antagonist activity is determined by looking at a wild type vascular endothelial growth factor (VEGF) or basic fibroblast growth factor (bFGF) activity and comparing the inhibition or reduction of such activity when the antagonist peptide is used. One can use any VEGF of bFGF activity. For example, analyzing the human umbilical vein endothelial cell (HUVEC) proliferation assay using VEGF or bFGF. Preferably, the portion has at least a 25% reduction in HUVEC proliferation, more preferably a 50% reduction, even more preferably a 75% reduction, most preferably a 95% reduction. Preferably, the peptide has a disulfide bond.

According to one embodiment herein, vascular endothelial growth factor (VEGF) antagonist activity of peptides is also be determined by inhibition of binding of labeled VEGF-A to VEGFR1 receptor and VEGFR2 receptors.

According to one embodiment herein, basic fibroblast growth factor (bFGF) antagonist activity of peptides is also be determined by inhibition of binding of labeled bFGF to bFGFR1 receptor.

According to one embodiment herein, the effectiveness of the basic fibroblast growth factor receptors and vascular endothelial growth factor receptor binding antagonistic peptide is analyzed in vitro and in vivo by a standard protocol or standard assays.

According to one embodiment herein, the effect of the growth factor antagonistic peptides on angiogenesis is analyzed by standard assays.

According to one embodiment herein, the VEGF antagonist peptide or bFGF antagonist peptides are used in preventing blinding blood vessel growth associated with diabetic eye diseases, namely diabetic retinopathy. The methods described herein are designed to antagonize VEGF, a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries.

According to one embodiment herein, the VEGF antagonist peptide or bFGF antagonist peptides are used in the treatment of age-related macular degeneration. As it is known that VEGF also contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macular.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1A:
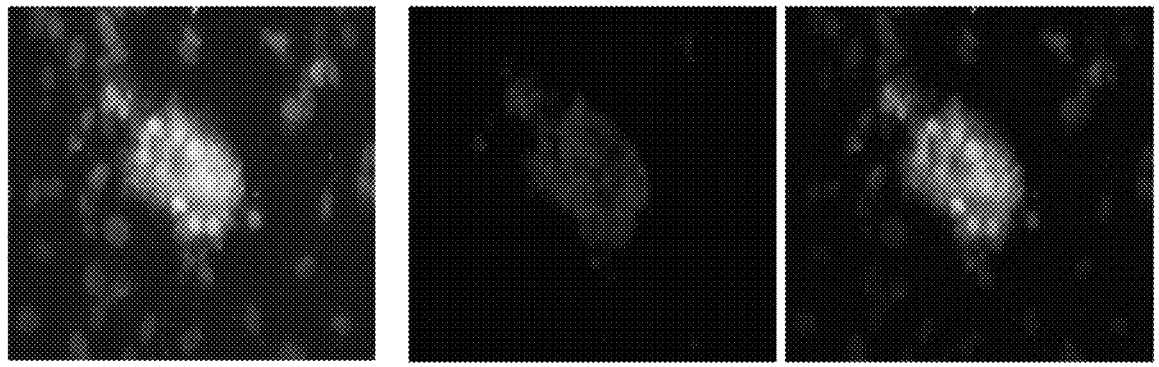
FIG. 1A-1B illustrates the results obtained after competitive binding assay of vascular endothelial growth factor (VEGF) antagonist VEGF-1, with VEGFR-1 (receptor) in Human Umbilical Vein Endothelial Cells (HUVECs), according to one embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein identify the portions of vascular endothelial growth factor (VEGF) and fibroblast growth factor (FGF) peptides which act as antagonist of VEGF-A, VEGF-B and bFGF respectively. The embodiments herein provide growth factor antagonist peptides of VEGF-A, VEGF-B and bFGF for treating the physiological conditions associated with angiogenesis and neovascularization. The embodiments herein provide peptide antagonists of VEGF-A, VEGF-B and bFGF for diagnosis of disease or condition which occur with over expression of VEGF and/or bFGF receptors.

According to one embodiment herein, a method for synthesizing antagonistic peptide for vascular endothelial growth factor (VEGF) and basic fibroblast growth factor (bFGF), comprises the following steps. The antagonistic peptides for vascular endothelial growth factor (VEGF) and basic fibroblast growth factor (bFGF) are synthesized by a protocol. The purity of the antagonistic peptide for vascular endothelial growth factor (VEGF) and basic fibroblast growth factor (bFGF) is analyzed by a protocol. A plurality of physico-chemical qualities of the antagonistic peptide for vascular endothelial growth factor (VEGF) and basic fibroblast growth factor (bFGF) are analyzed by a plurality of methods. The plurality of methods are HPLC chromatogram and Mass spectrometry analysis. The cyclization of peptides in the antagonistic vascular endothelial growth factor (VEGF) peptide and basic fibroblast growth factor (bFGF) peptide is analyzed by a protocol. The disulfide bond formation in the antagonistic peptide for vascular endothelial growth factor (VEGF) and basic fibroblast growth factor (bFGF) is analyzed by a protocol. The synthesized antagonistic peptide for vascular endothelial growth factor (VEGF) and basic fibroblast growth factor (bFGF) are annotated as Seq. ID No. 1 peptide, Seq. ID No. 2 peptide, Seq. ID No. 3 peptide, Seq. ID No. 4 peptide and Seq. ID No. 5 peptide. The Seq. ID No. 1 peptide, Seq. ID No. 2 peptide, Seq. ID No. 3 peptide are antagonists of both VEGF-A and VEGF-B. The Seq. ID No. 1 peptide, Seq. ID No. 2 peptide, Seq. ID No. 3 peptide in combination acts as antagonist for both VEGF-A and VEGF-B. The Seq. ID No. 4 peptide is antagonist of VEGF-A. The Seq. ID No. 5 peptide is antagonist of bFGF. The biochemical activity of the antagonistic peptide for vascular endothelial growth factor (VEGF) and basic fibroblast growth factor (bFGF) is analyzed by competitive binding assay, cell proliferation assay, Matrigel assay for anti-angiogenic activity analysis, histopathological staining and Western blot analysis.

According to one embodiment herein, the Seq. ID No. 1 peptide comprises a biochemical structure represented by 2HN-Cys-Gln-Val-Leu-Ile-Ser-Gln-Leu-Cys-COOH. The Seq. ID No. 1 comprises seven amino acid residues derived from VEGF-B (Gln46, Val48, Leu81, Ile83, Ser88, Gln89 and Leu90). The Seq. ID No. 1 comprises two Cys residues for chain cyclization. The Seq. ID No. 1 peptide binds and blocks vascular endothelial growth factor receptor-1 and vascular endothelial growth factor receptor-2 (VEGFR-1 and VEGFR-2).

According to one embodiment herein, the Seq. ID No. 2 peptide comprises amino acid residues derived from VEGF-B. The Seq. ID No. 2 comprises of amino acid residues 61-70 in VEGF-B. The Seq. ID No. 2 comprises a biochemical structure represented by 2HN-Cys61-Pro62-Asp63-Asp64-Gly65-Leu66-Glu67-Cys68-Val69-Pro70-COOH. The Seq. ID No. 2 peptide binds and blocks vascular endothelial growth factor receptor-1 and vascular endothelial growth factor receptor-2 (VEGFR-1 and VEGFR-2).

According to one embodiment herein, the Seq. ID No. 3 peptide comprises amino acid residues derived from VEGF-B. The Seq. ID No. 3 comprises of amino acid residues 101-105 in VEGF-B. The Seq. ID No. 3 comprises a biochemical structure represented by 2HN-Cys101-Glu102-Cys103-Arg104-Pro105-COOH. The Seq. ID No. 3 peptide binds and blocks vascular endothelial growth factor receptor-1 and vascular endothelial growth factor receptor-2 (VEGFR-1 and VEGFR-2).

According to one embodiment herein, the Seq. ID No. 4 peptide comprises amino acid residues derived from VEGF-A. The Seq. ID No. 4 comprises of amino acid residues 34-51 in VEGF-A. The Seq. ID No. 4 comprises a biochemical structure represented by 2HN-Asp34-Ile35-Phe36-Gln37-Glu38-Tyr39-Pro40-Asp41-Glu42-Ile43-Glu44-Tyr45-Ile46-Phe47-Lys48-Pro49-Ser50-Cys51-COOH. The cysteine residue is added optionally to the N-terminus of Seq. ID No. 4 for chain cyclization. The Seq. ID No. 4 peptide binds and blocks vascular endothelial growth factor receptor 2 (VEGFR-2).

According to one embodiment herein, Seq. ID No. 1 peptide, Seq. ID No. 2 peptide, Seq. ID No. 3 peptide and Seq. ID No. 4 peptide bind and block vascular endothelial growth factor receptors 1 (VEGFR-1) and/or vascular endothelial growth factor receptors 2 (VEGFR-2). The predetermined combination of Seq. ID No. 1 peptide, Seq. ID No. 2 peptide, Seq. ID No. 3 peptide and Seq. ID No. 4 peptide comprising a disulfide bond bind and block vascular endothelial growth factor receptors 1 (VEGFR-1) and/or vascular endothelial growth factor receptors 2 (VEGFR-2).

According to one embodiment herein, the Seq. ID No. 5 peptide comprises amino acid residues derived from bFGF. The Seq. ID No. 5 comprises a biochemical structure represented by 2HN-Leu119-Lys120-Arg121-Thr122-Gly123-Gln124-Tyr125-Lys126 Leu127-COOH. A plurality of cysteine residues are added optionally to the N-terminus and C-terminus of Seq. ID No. 5 for chain cyclization. Cysteine residues are added to the N-terminus and C-terminus of Seq. ID No. 5 to obtain a biochemical structure represented by 2HN-Cys-Leu-Lys-Arg-Thr-Gly-Gln-Tyr-Lys-Leu-Cys-COOH (Seq. Id. No. 6). The Seq. ID No. 5 peptide binds and blocks basic fibroblast growth factor-receptors 1 (bFGFR-1). The Seq. ID No. 5 peptide binds and blocks vascular endothelial growth factor receptor 1 (VEGFR-1) and/or vascular endothelial growth factor receptor2 (VEGFR-2) and basic fibroblast growth factor-receptor 1 (bFGFR-1) with a predetermined combination of Seq. ID No. 5 peptide and with at least one of Seq. ID No. 1 to Seq. ID No. 4.

According to one embodiment herein, antagonistic peptide for vascular endothelial growth factor (VEGF) and basic fibroblast growth factor (bFGF) comprises amino-acids residues in a range of 5 to 54 amino acids or a segment thereof. The antagonistic peptide for vascular endothelial growth factor (VEGF) and basic fibroblast growth factor (bFGF) binds and blocks vascular endothelial growth factor receptors 1 and/or 2 (VEGFR-1 and VEGFR2) and/or basic fibroblast growth factor-receptors 1 and/or 2 (bFGFR-1 and bFGFR-2). The antagonistic peptide for vascular endothelial growth factor (VEGF) and basic fibroblast growth factor (bFGF) Seq. ID No. 1-Seq. ID No. 5 are with or without an additional disulfide bond. The antagonistic peptide for vascular endothelial growth factor (VEGF) and basic fibroblast growth factor (bFGF) Seq. ID No. 1-Seq. ID No. 5 peptides comprises a plurality of diagnostic, therapeutic and theranostic properties. The plurality of diagnostic, therapeutic and theranostic properties of Seq. ID No. 1-Seq. ID No. 5 peptides is induced by a plurality of amino acid substitutions and a plurality of different amino acid positions.

According to one embodiment herein, a plurality of diagnostic, therapeutic and theranostic properties of Seq. ID No. 1-Seq. ID No. 5 peptides is observed in VEGF and bFGF antagonistic sequences comprising a sequence similarity of more than 70% with a parent peptide sequence. The diagnostic, therapeutic and theranostic properties of Seq. ID No. 1-Seq. ID No. 5 peptides is observed in VEGF and bFGF antagonistic sequences along with a pharmaceutically acceptable carrier. The Seq. ID No. 1-Seq. ID No. 5 peptides are linked to a heterologous peptide and/or protein. The theranostic property is used for topically administrating a plurality of therapeutic compositions. The plurality of therapeutic compositions comprise cream, lotion, solution and lip balm.

According to one embodiment herein, the Seq. ID No. 1-Seq. ID No. 5 peptides illustrate anti-angiogenesis activity. The Seq. ID No. 1-Seq. ID No. 5 peptides are useful for treatment of an angiogenesis-related disease. The angiogenesis-related disease is selected from the group consisting of cancer, ascites formation, psoriasis, age-related macular degeneration, thyroid hyperplasia, preeclampsia, rheumatoid arthritis and osteoarthritis, Alzheimer's disease, obesity, pleura effusion, atherosclerosis, endometriosis, diabetic/other retinopathies, neovascular glaucoma, age-related macular degeneration, hemangiomas, and corneal neovascularization.

According to one embodiment herein, the competitive binding assay of antagonistic peptide for vascular endothelial growth factor (VEGF) and basic fibroblast growth factor (bFGF) binds with the cell receptors at a concentration of 2000 ng/ml. The cell proliferation assay illustrates that the cell growth is arrested when the antagonistic peptide for vascular endothelial growth factor (VEGF) and basic fibroblast growth factor (bFGF) are at a concentration of 2000 ng/ml. The anti-angiogenic activity result analysis illustrates that the angiogenesis in the cells is arrested when the concentration of antagonistic peptide for vascular endothelial growth factor (VEGF) and basic fibroblast growth factor (bFGF) is 2000 ng/ml.

Experiment-1 Synthesis of Antagonist Peptide for Vascular Endothelial Growth Factor (VEGF) and Fibroblast Growth Factor (FGF)

The antagonist peptide for VEGF and FGF are synthesized by using standard protocol disclosed by Shine Gene Bio-Technologies, Inc. Shanghai, China. The purity of antagonist peptide for VEGF and FGF is 90%. The quality of the synthesized peptides is confirmed by HPLC chromatogram, Mass spec analysis, and synthesis report for every peptide. The peptide cyclization is verified by the manufacturer. Further the disulfide bond formation is verified by a standard protocol.

According to one embodiment herein, the antagonist peptide for VEGF and FGF are synthesized and annotated as Seq. ID No. 1-Seq. ID No. 5.

According to one embodiment herein, Seq. ID No. 1 is identified as 2HN-Cys-Gln-Val-Leu-Ile-Ser-Gln-Leu-Cys-COOH. Seq. ID No. 1 consists of seven residues derived from VEGF-B (Gln46, Val48, Leu81, Ile83, Ser88, Gln89 and Leu90) and two Cys residues for chain cyclization.

Seq. ID No. 2 consists of residues 61-70 in VEGF-B; 2HN-Cys61-Pro62-Asp63-Asp64-Gly65-Leu66-Glu67-Cys68-Val69-Pro70-COOH.

Seq. ID No. 3 consists of residues 101-105 in VEGF-B; 2HN-Cys101-Glu102-Cys103-Arg104-Pro105-COOH.

Seq. ID No. 4 consists of residues 34-51 in VEGF-A; 2HN-Asp34-Ile35-Phe36-Gln37-Glu38-Tyr39-Pro40-Asp41-Glu42-Ile43-Glu44-Tyr45-Ile46-Phe47-Lys48-Pro49-Ser50-Cys51-COOH. A cysteine residue may be added to the N-terminus of Seq. ID No. 4 for chain cyclization.

Seq. ID No. 5 consists of 2HN-Leu119-Lys120-Arg121-Thr122-Gly123-Gln124-Tyr125-Lys126-Leu127-COOH and two cysteine residues at N- and C-terminals for chain cyclization. Accordingly, the sequence of Seq. ID No. 6 is 2HN-Cys-Leu-Lys-Arg-Thr-Gly-Gln-Tyr-Lys-Leu-Cys-COOH.

According to one embodiment herein, the residues of Seq. ID No. 1, are derived from a specific residue in VEGF-B. The residues of Seq ID No. 1 mimic a receptor-binding pocket of VEGF-B composed of residues 46-48 and 81-90 that are located in the vicinity of each other in the 3D structure. The remaining Seq ID's are derived from a fragment of a growth factor. The Seq ID No. 2 and Seq ID No. 3 are derived from VEGF-B. The Seq ID No. 4 is derived from VEGF-A. The Seq ID No. 5 is derived from bFGF. This illustrates that the parental sequence is changed in Seq. ID No. 1 but not in the other Seq. ID's. However, each peptide sequence comprises a disulfide bond. The disulfide bond is either formed by Cys residues that are present in the native sequence or artificially made by addition of Cys residues somewhere in the sequence.

According to one embodiment herein, all of the antagonist peptide for VEGF and FGF have antagonistic properties.

The Seq ID No. 1, 2 and 3, each alone or in combination are antagonists of both VEGF-A and VEGF-B. The Seq. ID No. 4 is antagonist of VEGF-A. The Seq. ID No. 5 is antagonist of bFGF.

Experiment-2 Analysis of Antagonist Activity of Peptide Sequences of Vascular Endothelial Growth Factor (VEGF) [Seq ID No. 1-Seq ID No. 4]

Binding Assay—To assess competitive binding assay of VEGF antagonists, Human Umbilical Vein Endothelial Cells (HUVECs) are cultured in 96-well plates (5000 cells/well) with Dulbecco's Modified Eagle Medium (DMEM) and 5% FBS incubated at 37° C. for overnight. After 24 h, the media of cells are changed with DMEM medium without fetal bovine serum (FBS) and the cells are treated (except the control) with 1000-2000 ng/ml the peptides at 37° C. for overnight. The cells are fixed by paraformaldehyde 4% at room temperature for 5-10 min. After 5-10 min the cells are rinsed with phosphate buffer saline (PBS) and permeabilized with PBS+0.3% Triton X-100. The cells are then blocked with 10% normal goat serum, BSA 1%/PBST for 20 minutes in the room temperature and followed by PE-conjugated anti-VEGFR-1 antibody (5000 ng/ml, Ab208739). After subjecting cells to blocking and Phycoerythrin (PE) conjugated anti-VEGFR-1 antibody the cells are subjected to washing with PBS. The cells are then mounted with 4', 6-diamidino-2-phenylindole (DAPI) (Invitrogen, Carlsbad, Calif.) (1 µg/mL), anti-VEGFR-2 antibody (5000 ng/ml, Ab39256) with FITC-secondary (Ab6717) antibody and stained with propidium iodide (Sigma Aldrich, USA, P4170) (1 µg/ml) for nuclear staining. For further probing the dual receptor binding, a mixture of soluble anti-VEGFR-1 (5000 ng/ml, Ab208739) and anti-VEGFR-2 (5000 ng/ml, Ab1316) are added to 5000 HUVEC cells and incubated at 4° C. for overnight and 2 h, respectively. After 24 hours and 2 hours the cells are washed in PBS and labeled with a 1:200 dilution of FITC-secondary anti-mouse antibody (Ab6717) for 20 min at 4° C. The cells are captured by fluorescence microscope in blue (DAPI, Invitrogen, Carlsbad, Calif., 1 µg/ml, nuclear staining), red (PE-conjugated), green (VEGFR-2/FITC-secondary anti-mouse) and merged then analyzed by NIH Image J software.

Cell Proliferation Assay—The effect of VEGF antagonists on VEGF-induced proliferation of HUVECs is quantified after 24 h by 3-(4, 5-dimethylthiazolyl-2)-2,5-diphenyltetrazolium bromide (MTT) (Sigma Aldrich, USA) assay. The absorbance is measured at 570 nm with background subtraction of 630 nm using the ELISA reader (Space fax 2100, Awareness, USA). Briefly, 2×103 HUVECs are added to each well of a plate in Dulbecco's Modified Eagle Medium (DMEM) media comprising 5% fetal bovine serum (FBS), incubated overnight at 37° C. The cells are then transferred to serum-free DMEM medium, and VEGF-A at 37° C., 5% CO2. Alternatively, the cells are treated with varying concentrations of VEGF antagonists (100-2000 ng/mL) and VEGF-A (200 ng/ml) for 48 h at 37° C. and 5% CO2. Un-stimulated and VEGF-stimulated cells are used as negative and positive controls, respectively. The data obtained is assessed against the 200 ng/ml VEGF-stimulated positive control and analyzed by NIH Image J software. The error bars represent the standard deviation of measurements performed in triplicate.

Tube Formation Assay 2D Model—Matrigel matrix (50 µL/well) is added into 96-well culture plates. The 96-well culture plates are incubated for 30 min at 37° C., and 50 µl is added to each well of a microtiter plate and allowed to solidify for 10 min at 37° C. The 96-well plates are incubated with 2×103 HUVECs with 200 ng/ml VEGF-A and varying concentrations of VEGF antagonists for 14-18 h at 37° C. and 5% CO2. Cells were washed in PBS and the tube formation was observed under an inverted microscope. Thread network formation and number of the branch points was quantified by analysis of images using Image J software to determine the extent of capillary-like structures. Data was normalized against 200 ng/ml VEGF-A-stimulated positive control.

In vivo Tumor Growth Regression-Animal studies are conducted according to relevant national and international guidelines of the Weatherall report and Institutional Animal Care and Use Committee (IACUC) of Tehran University of Medical Sciences. The tumors induced in the female BALB/c mice (5 weeks old) are purchased from the Laboratory Animal Center of Iran Pasteur Institute and maintained under 12 h dark and light cycle. The 4T1 tumor model mouse are sterilized and established from the breast cancer bearing BALB/c mice by a standard protocol. The 4T1 tumor model mouse are prepared by cutting the tumor into pieces of <0.3 cm3. The tumor pieces are subcutaneously transplanted into the left flank of the mouse under ketamine (100 mg/kg, i.p.) and xylazine (10 mg/kg, i.p.) anesthesia. The mouse carrying tumors with a tumor size reaching to 400 mm3 are randomized and divided into groups. Each group of tumor induced mice comprises 6 mouse. The first group is treated with vascular endothelial growth factor (VEGF). The second group is treated with phosphate buffer saline. The first group or treated groups receives daily 1, 2.5 and 10 mg/kg i.p. of VEGF-antagonistic peptides compared to PBS control group for two weeks. The tumor volume is measured every two days by a digital Vernier caliper (Mitutoyo, japan), using the following formula: $v=a2×b×0.52$ (where "a" is the shortest and "b" is the longest diameter).

Histopathological analyses—The excised tumor tissues are fixed in formalin (4%), embedded in paraffin, sectioned and stained against CD31, CD34, Ki-67, P53, Bcl-2 and TUNEL. The CD31 and CD34 staining is performed to assigned microvascular density (MVD). To count microvessels of the murine breast cancer tissue, the 5 randomly selected vascularized areas are counted under scale bar 100 and 20 μm. The microvascular density (MVD) of the tumor is measured and evaluated by the standard protocol. The microvessels are manually counted on the images at scale bar of 20 μm. The MVD is calculated as the mean of five hot spot areas as CD31 and CD34-positive vessels under scale bar 20 μm. Cell proliferation in the tumor is determined by staining histologic sections of tumor with monoclonal antibodies (mAbs) against Ki67 (Dako, Denmark). The Ki67 is a nuclear protein expressed in proliferating cells. The data obtained is presented by percentage of Ki67-positive cells at a scale bar of 20 μm.

The apoptosis is determined by terminal uridine deoxynucleotidyl transferase dUTP nick end labeling (TUNEL) assay (using an in situ Cell Death Detection Kit POD (Roche Diagnostic GmbH, Germany)), p53 and anti-apoptotic Bcl-2 in a at scale bar: 20 μm. The data obtained is reported as percentage apoptosis cells/total cells. Subsequent DAB (Invitrogen, Carlsbad, Calif.) detection is performed and images are acquired by microscope (Olympus BX-51, Japan).

The tumor tissues from control and peptide-treated (cultured cells or mice) are lysed with RIPA lysis buffer. The RIPA lysis buffer consists of 50 mM Tris-HCl, pH 8.0, 150 mM NaCl, 1.0% NP-40, 0.5% sodium deoxycholate, and 0.1% sodium dodecyl sulfate (SDS)) containing protease inhibitor cocktail and phosphatase inhibitor cocktail 3 (Sigma, St. Louis, Mo., USA) (23,24). Protein concentrations are assessed by Bradford assay. Equal amounts of protein are resolved using 10% SDS-polyacrylamide gel electrophoresis and transferred to Amersham™ Protran® Premium nitrocellulose western blotting membranes (Ge10600013, Sigma, St. Louis, Mo., USA). The following primary antibodies are added to the membranes with 5% dry milk in Tris-buffered saline and Tween 20 (TBST) overnight at 4° C.: anti-AKT, anti-AKT phospho 5473, anti-p44/p42 MAPK (ERK1/2), phospho-p44/p42 MAPK (ERK1/2).

The premium nitrocellulose western blotting membranes are washed with TBST and incubated with horseradish peroxidase-conjugated goat anti-mouse IgG secondary antibody. GAPDH is used as the loading control, and proteins are visualized using a chemiluminescence detection system (Amersham ECL™ Select western blotting detection kit; GE Healthcare, Little Chalfont, UK) according to the manufacturer's protocol (GERPN2236). The quantitative analysis of protein expression to the reference protein, repeated at least three times, is performed using ImageJ.

Experiment-3 Analysis of Antagonist Activity of Peptide Sequences of Basic Fibroblast Growth Factor (bFGF) [Seq ID No. 5]

According to one embodiment herein, the Seq. ID No. 5 is antagonist of bFGF. This peptide recognizes bFGFR.

Binding Assay—To assess competitive binding assay of bFGF antagonist, Human Umbilical Vein Endothelial Cells (HUVECs) are cultured in 96-well plates (5000 cells/well) with DMEM and 5% fetal bovine serum (FBS) incubated at 37° C. for overnight. After 24 h, the media in the 96-well plates is changed with DMEM without FBS and the cells are treated (except the control 96-well plates) with 1000-2000 ng/ml the peptides at 37° C. for overnight. The cells are fixed by 4% paraformaldehyde at room temperature for 5-10 min. After 5-10 minutes the cells are rinsed with phosphate buffer saline (PBS), permeabilized with PBS+0.3% Triton X-100. The growth of cells is inhibited with a mixture comprising 10% normal goat serum, bovine serum albumin (BSA) 1% PBST for 20 minutes in the room temperature. After 20 minutes the cells are subjected to anti-FGFR-1 (5000 ng/ml, Ab10646) with FITC-secondary (Ab6717) antibody and stained with propidium iodide (Sigma Aldrich, USA, P4170) (1 μg/ml) for nuclear staining. The cell-binding is analyzed by NIH Image J software.

Cell Proliferation Assay—To analyze the ability of basic fibroblast growth factor (bFGF) antagonist peptide to inhibit the bFGF-induced cell proliferation, the ovarian cell line SKOV3 is utilized. The SKOV3 cell line is found to be dependent on bFGF for cellular proliferation. For cell culture, SKOV3 cells are maintained in DMEM supplemented with 5% FBS, 1% streptomycin, penicillin, 2 nM glutamine and is *mycoplasma* free.

For estimating the anti-proliferative activity of bFGF, SKOV3 is plated at 1×104 cell per well in a 24 well dish in 1 ml DMEM, the cells are maintained in DMEM and treated with human recombinant bFGF (hr-bFGF) (0-100 ng/ml) alone and in combination with different concentration of the antagonistic peptide (25-1000 ng/ml) every other day for total 5-6 days. The experiment is terminated when cells are in confluence. The MTT assay is performed. The absorbance is determined at 540 nm. The results are expressed as the mean of triplicate experiments (+SD). One-way analysis of variance is used to determine significance.

According to one embodiment herein, in vitro tube formation assay and in vitro tumor growth regression, histopathological analysis and Western Blot Analysis are performed in the similar experimental condition as VEGF-antagonists.

According to one embodiment herein, angiogenesis is an integral part of formation of the inflammatory pannus and without angiogenesis, leukocyte ingress cannot occur. The disruption of formation of new blood vessel not only prevents delivery of nutrients to the inflammatory site, but also reduces the joint swelling due to the additional activity of VEGF, which is a potent pro-angiogenic factor in rheumatoid arthritis, as a vascular permeability factor. Vascular endothelial growth factor (VEGF) and receptors VEGFR-1 (Flt1) and VEGFR-2 (KDR), have been analyzed in psoriatic arthritis (PsA) synovial tissue. The analysis illustrates VEGF's role in inducing angiogenesis and vascular permeability. Flt-1 is expressed not only in vascular endothelial cells but also in macrophage lineage cells and regulates VEGF oriented migration, survival and angiogenic factor production. Using the wild type and Flt-1 TK−/− mice, inflammatory responses, such as immune cell infiltration, angiogenesis and edema in the knee joints are found to be significantly weaker in TK−/− mice than in wild type mice in a rheumatoid arthritis (RA) model. These results illustrate that the TK signaling of Flt-1 is a potential target for treatment of cancer and rheumatoid arthritis.

According to one embodiment herein, the invention provides a method of treating an angiogenic disease or disorder, comprising administering to a subject in need thereof a vector comprising a polynucleotide encoding a basic fibroblast growth factor (bFGF) receptor or vascular endothelial growth factor (VEGF) receptor binding peptide. Alternatively, a pharmaceutical composition comprising a FGF-R and/or VEGF-R binding peptide and a pharmaceutically acceptable carrier is administered. In one embodiment, the said subject in need of treatment is a mammal, such as a dog or a cat, preferably a human.

According to one embodiment herein, a method is provided for treating an angiogenesis-related disease or disorder, comprising administering to a subject in need thereof a pharmaceutical composition comprising a FGF- and/or VEGF-R binding peptide. In another embodiment, the methods described herein are used in combination with other treatment options available for angiogenesis-related diseases or disorders.

According to one embodiment herein, angiogenesis refers to the sprouting of new blood vessels from pre-existing blood vessels, characterized by endothelial cell proliferation and migration triggered by certain pathological conditions, such as the growth of solid tumors and metastasis.

According to one embodiment herein, the term "angiogenesis-related disease or disorder" refers to diseases or disorders which are dependent on a rich blood supply and blood vessel proliferation for the disease's pathological progression (example—metastatic tumors) or diseases or disorders that are the direct result of aberrant blood vessel proliferation (e.g. diabetic retinopathy and hemangiomas). Examples include abnormal vascular proliferation, ascites formation, psoriasis, age-related macular degeneration, thyroid hyperplasia, preclampsia, rheumatoid arthritis and osteo-arthritis, Alzheimer's disease, obesity, pleural effusion, atherosclerosis, endometriosis, diabetic/other retinopathies, ocular neovascularization such as neovascular glaucoma and corneal neovascularization.

According to one embodiment herein, for example the angiogenesis-related disease or disorder are cancer, ascites formation, psoriasis, age-related macular degeneration, thyroid hyperplasia, preclampsia, rheumatoid arthritis and osteoarthritis, Alzheimer's disease, obesity, pleura effusion, atherosclerosis, endometriosis, diabetic/other retinopathies, neovascular glaucoma, age-related macular degeneration, hemangiomas, and corneal neovascularization. The age-related macular degeneration is wet macular degeneration.

According to one embodiment herein, the angiogenesis-related disease or disorder is cancer. In cancer the rapidly dividing neoplastic cancer cells require an efficient blood supply to sustain their continual growth of the tumor. The cancer refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of a polynucleotide encoding a fibroblast growth factor (FGF) receptor, vascular endothelial growth factor (VEGF) receptor binding peptide or a pharmaceutical composition comprising a FGF- or VEGF-R binding peptide and a pharmaceutically acceptable carrier inhibits angiogenesis. By inhibiting angiogenesis at the primary tumor site and secondary tumor site, embodiments of the invention serve to prevent and limit the progression of the disease.

According to one embodiment herein, the solid tumor requires an efficient blood supply for cell growth and cell division. The tumors requiring blood supply are carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermato-fibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

According to one embodiment herein, the growth factor peptide antagonists can be used in preventing blinding blood vessel growth associated with diabetic eye diseases, namely diabetic retinopathy.

According to one embodiment herein, the methods are designed to antagonize vascular endothelial growth factor (VEGF), a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, if the backup blood vessels are faulty; they leak, bleed and encourage scar tissue that detaches the retina, resulting in severe loss of vision. Such growth is the hallmark of diabetic retinopathy, the leading cause of blindness among young people in developed countries.

According to one embodiment herein, the growth factor peptide antagonists can be used in the treatment of age-related macular degeneration, as it is known that VEGF also contributes to abnormal blood vessel growth from the choroid layer of the eye into the retina, similar to what occurs during the wet or neovascular form of age-related macular degeneration. Macular degeneration, often called age-related macular degeneration (AMD or ARMD), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula.

According to one embodiment herein, the angiogenesis-related disease or disorder is rheumatoid arthritis. Rheumatoid arthritis (RA) is characterized by synovial tissue swelling, leucocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognized as a key event in the formation and maintenance of the pannus in RA. Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur. Disruption of the formation of new blood vessels would not only prevent delivery of nutrients to the inflammatory site, it could also reduce joint swelling due to the additional activity of VEGF, a potent pro-angiogenic factor in RA, as a vascular permeability factor. VEGF and its receptors, VEGFR-1/Flt1 and VEGFR-2/KDR, have been demonstrated in psoriatic arthritis (PsA) synovial tissue, suggesting VEGF's role in inducing angiogenesis and vascular permeability. Flt-1 is expressed not only in vascular endothelial cells but also in macrophage lineage cells and regulates VEGF oriented migration, survival, and angiogenic factor production. Using the wild-type and Flt-1 TK−/− mice, inflammatory responses such as immune cell infiltration, angiogenesis, and edema in the knee joints are found to be significantly weaker in TK−/− mice than in wild-type mice in a rheumatoid arthritis (RA) model. Taken together, these results suggest that the TK signaling of Flt-1 is a potential target for treatment of cancer and RA.

Figure 1B:
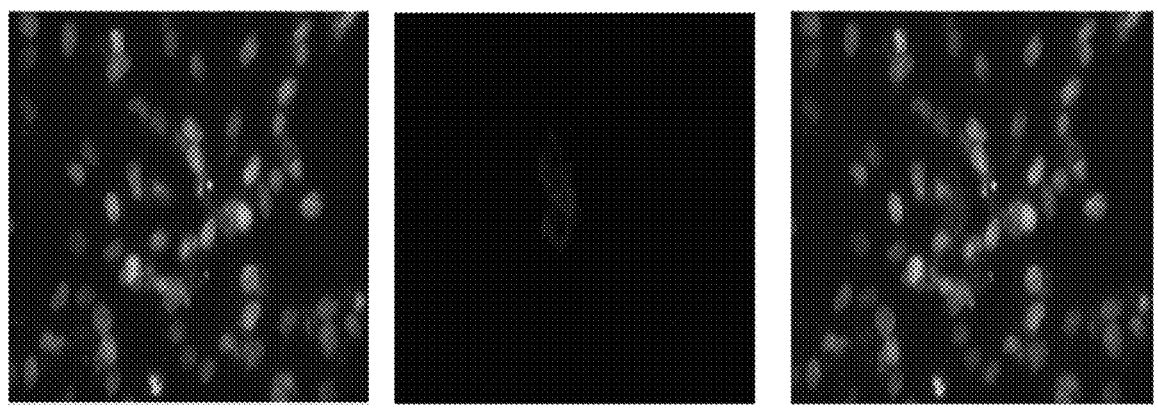

FIG. 1A-1B illustrates the results obtained after competitive binding assay of vascular endothelial growth factor (VEGF) antagonist VEGF-1, with VEGFR-1 (receptor) in Human Umbilical Vein Endothelial Cells (HUVECs), according to one embodiment herein. FIG. 1A illustrates the control for the competitive binding assay of vascular endothelial growth factor (VEGF) antagonist VEGF-1, with VEGFR-1 (receptor) in Human Umbilical Vein Endothelial Cells (HUVECs). FIG. 1B illustrates the assay results where the concentration of the VEGF-1 peptide antagonist is 2000 ng/ml in the assay culture medium.

Figure 1C:
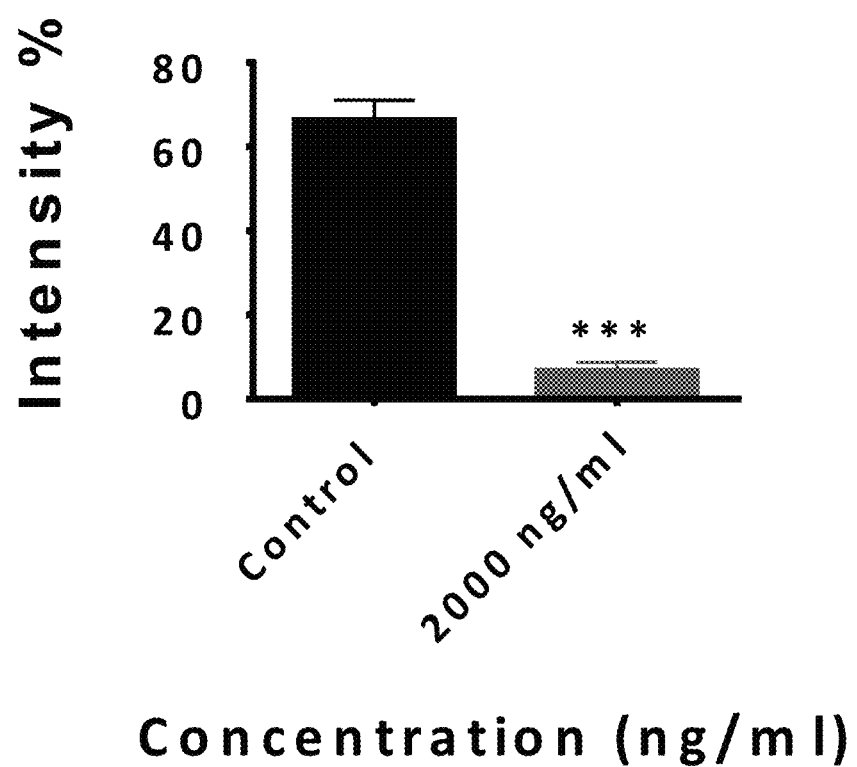
FIG. 1C is a bar graph illustrates the results obtained after competitive binding assay of vascular endothelial growth factor (VEGF) antagonist VEGF-1, with VEGFR-1 (receptor) in Human Umbilical Vein Endothelial Cells (HUVECs), according to one embodiment herein.

FIG. 1C is a bar graph illustrates the results obtained after competitive binding assay of vascular endothelial growth factor (VEGF) antagonist VEGF-1, with VEGFR-1 (receptor) in Human Umbilical Vein Endothelial Cells (HUVECs), according to one embodiment herein. The concentration of the VEGF-1 peptide antagonist is 2000 mg/ml in the assay culture medium for binding with the VEGFR-1 (receptor).

Figure 2A:
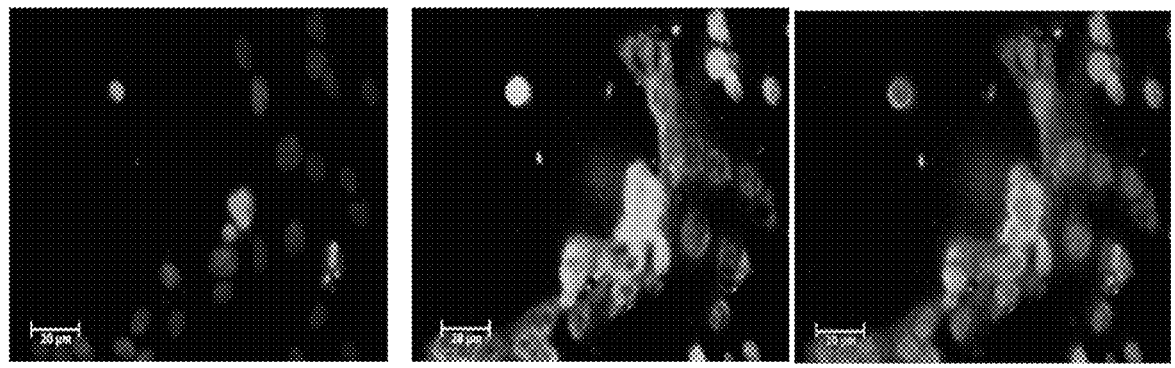
FIG. 2A-2B illustrates the results obtained after competitive binding assay of vascular endothelial growth factor (VEGF) antagonist VEGF-1, with VEGFR-2 (receptor) in Human Umbilical Vein Endothelial Cells (HUVECs), according to one embodiment herein.
Figure 2B:
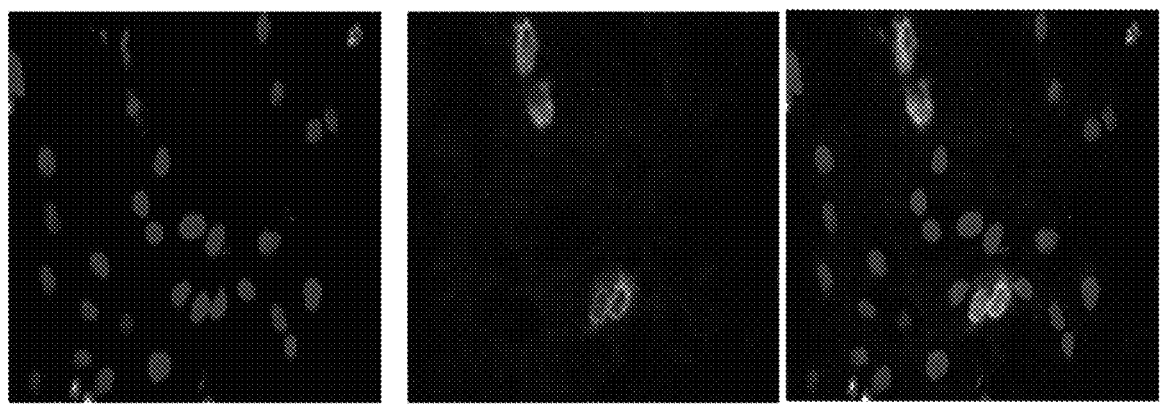

FIG. 2A-2B illustrates the results obtained after competitive binding assay of vascular endothelial growth factor (VEGF) antagonist VEGF-1, with VEGFR-2 (receptor) in Human Umbilical Vein Endothelial Cells (HUVECs), according to one embodiment herein. FIG. 2A illustrates the control for the competitive binding assay of vascular endothelial growth factor (VEGF) antagonist VEGF-1, with VEGFR-2 (receptor) in Human Umbilical Vein Endothelial Cells (HUVECs). FIG. 2B illustrates the assay results where the concentration of the VEGF-1 peptide antagonist is 2000 ng/ml in the assay culture medium.

Figure 2C:
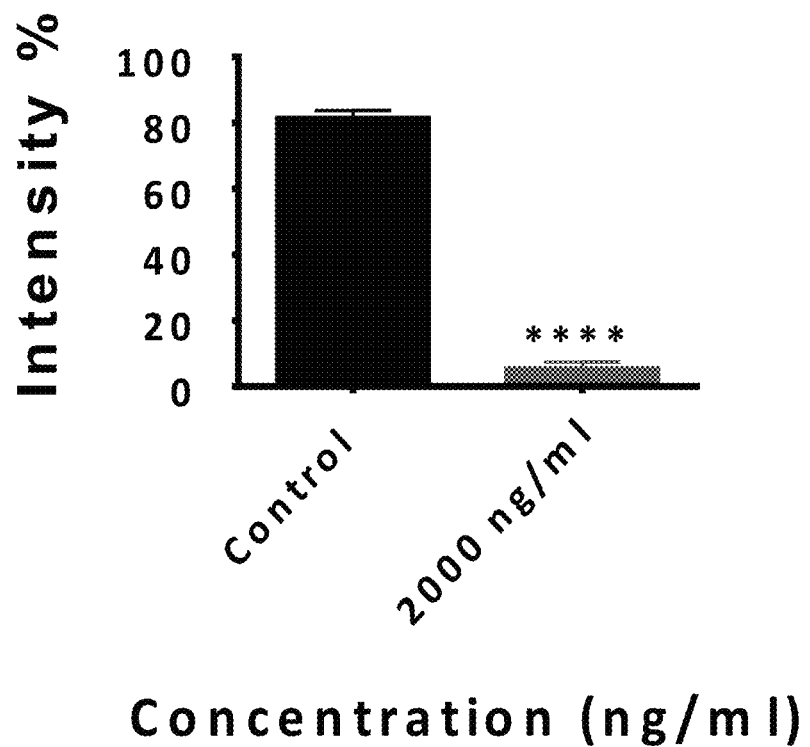
FIG. 2C is a bar graph illustrating the results obtained after competitive binding assay of vascular endothelial growth factor (VEGF) antagonist VEGF-1, with VEGFR-2 (receptor) in Human Umbilical Vein Endothelial Cells (HUVECs), according to one embodiment herein.

FIG. 2C is a bar graph illustrating the results obtained after competitive binding assay of vascular endothelial growth factor (VEGF) antagonist VEGF-1, with VEGFR-2 (receptor) in Human Umbilical Vein Endothelial Cells (HUVECs), according to one embodiment herein. The concentration of the VEGF-1 peptide antagonist is 2000 ng/ml in the assay culture medium for binding with the VEGFR-2 (receptor).

Figure 3A:
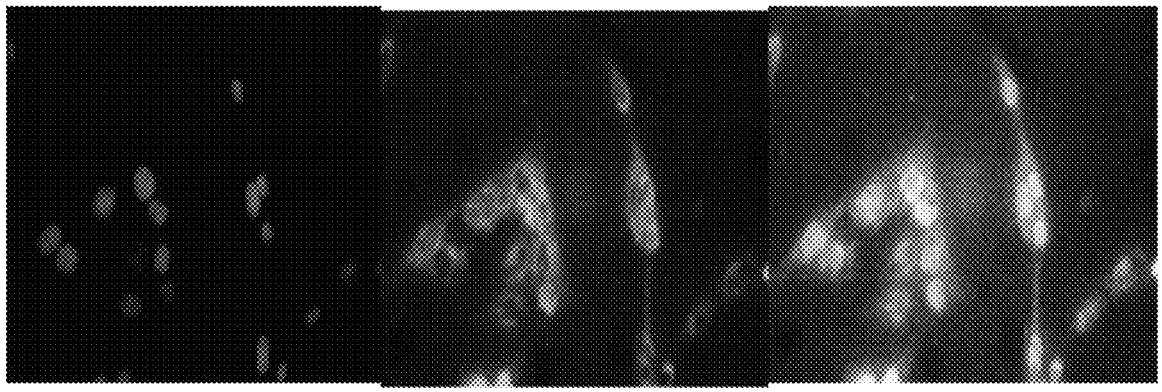
FIG. 3A-3B illustrates the results obtained after competitive binding assay of basic fibroblast growth factor (bFGF) antagonist bFGF-1, with bFGFR-1 (receptor) in Human Umbilical Vein Endothelial Cells (HUVECs), according to one embodiment herein.
Figure 3B:
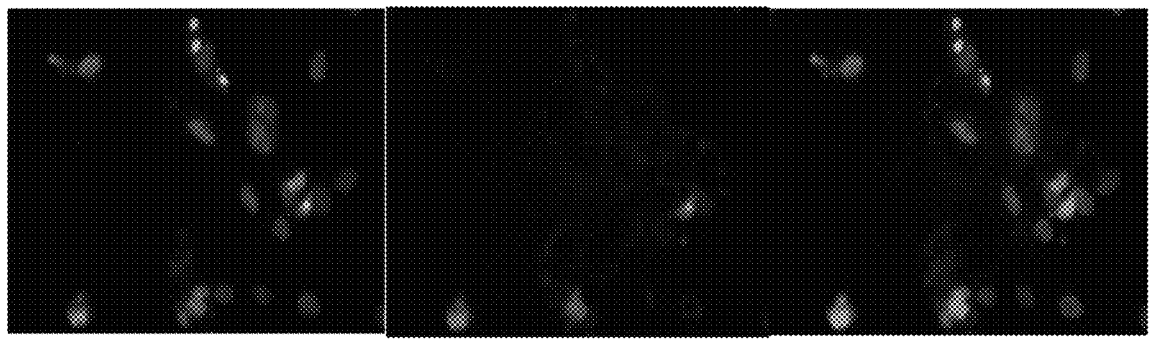

FIG. 3A-3B illustrates the results obtained after competitive binding assay of basic fibroblast growth factor (bFGF) antagonist bFGF-1, with bFGFR-1 (receptor) in Human Umbilical Vein Endothelial Cells (HUVECs), according to one embodiment herein. FIG. 3A illustrates the control for the competitive binding assay of basic fibroblast growth factor (bFGF) antagonist bFGF-1, with bFGFR-1 (receptor) in Human Umbilical Vein Endothelial Cells (HUVECs). FIG. 3B illustrates the assay results where the concentration of the bFGF-1 peptide antagonist is 2000 ng/ml in the assay culture medium.

Figure 3C:
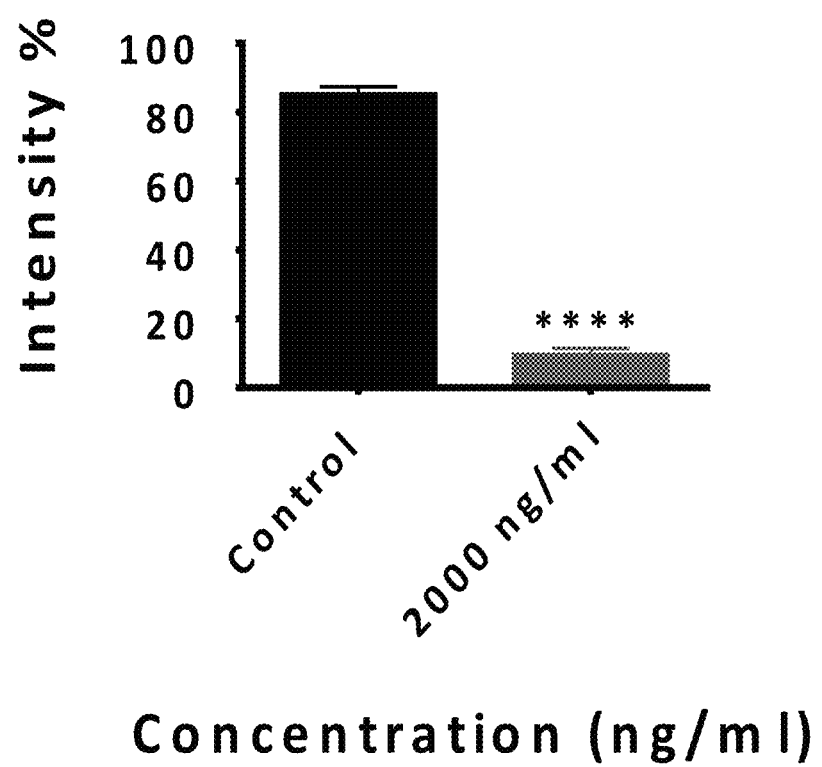
FIG. 3C is a bar graph illustrating the results obtained after competitive binding assay of basic fibroblast growth factor (bFGF) antagonist bFGF-1, with bFGFR-1 (receptor) in human umbilical vein endothelial cells (HUVECs), according to one embodiment herein.

FIG. 3C is a bar graph illustrating the results obtained after competitive binding assay of basic fibroblast growth factor (bFGF) antagonist bFGF-1, with bFGFR-1 (receptor) in Human Umbilical Vein Endothelial Cells (HUVECs), according to one embodiment herein. The concentration of the bFGF-1 peptide antagonist is 2000 ng/ml in the assay culture medium for binding with the bFGFR-1 (receptor).

Figure 4A:
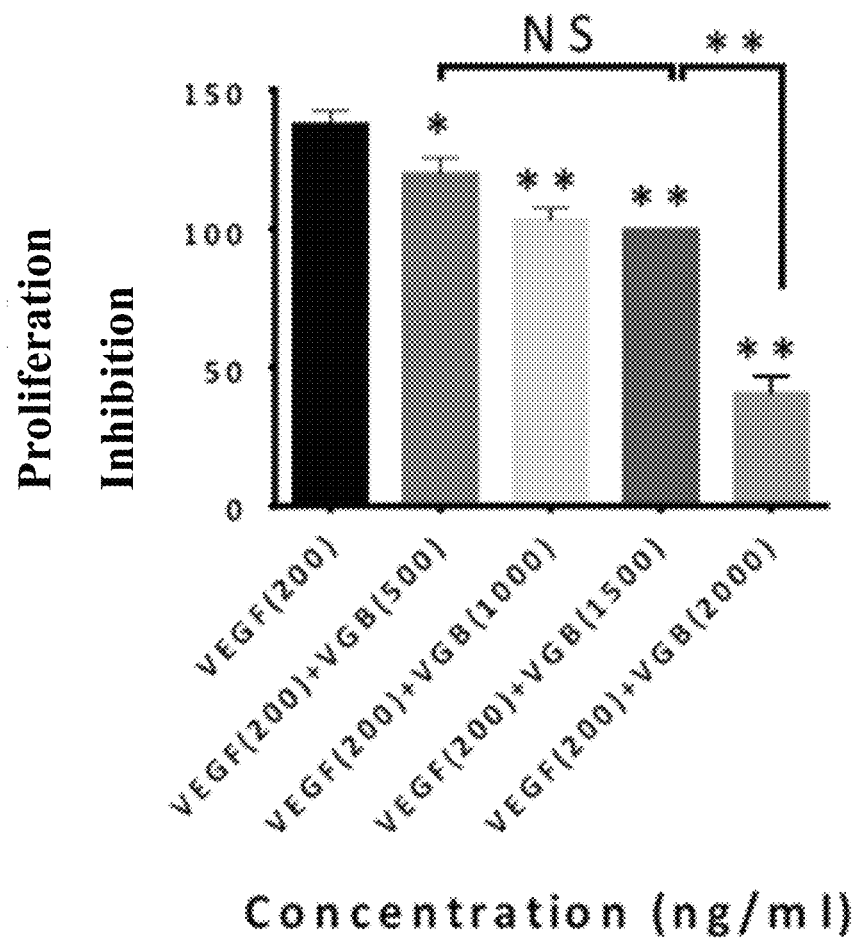
FIG. 4A is a bar graph illustrating the results obtained from the human umbilical vein endothelial cells (HUVECs) proliferation assay in presence of vascular endothelial growth factor (VEGF) antagonist, according to one embodiment herein.

FIG. 4A is a bar graph illustrating the results obtained from the Human Umbilical Vein Endothelial Cells (HUVECs) proliferation assay in presence of vascular endothelial growth factor (VEGF) antagonist, according to one embodiment herein. The bar graph illustrate that VEGF antagonist peptide inhibits the VEGF-A induced proliferation of HUVECs in a dose dependent manner. FIG. 4A illustrates that when the concentration of the VEGF antagonist peptide is 2000 ng/ml, then the cell proliferation is reduced.

Figure 4B:
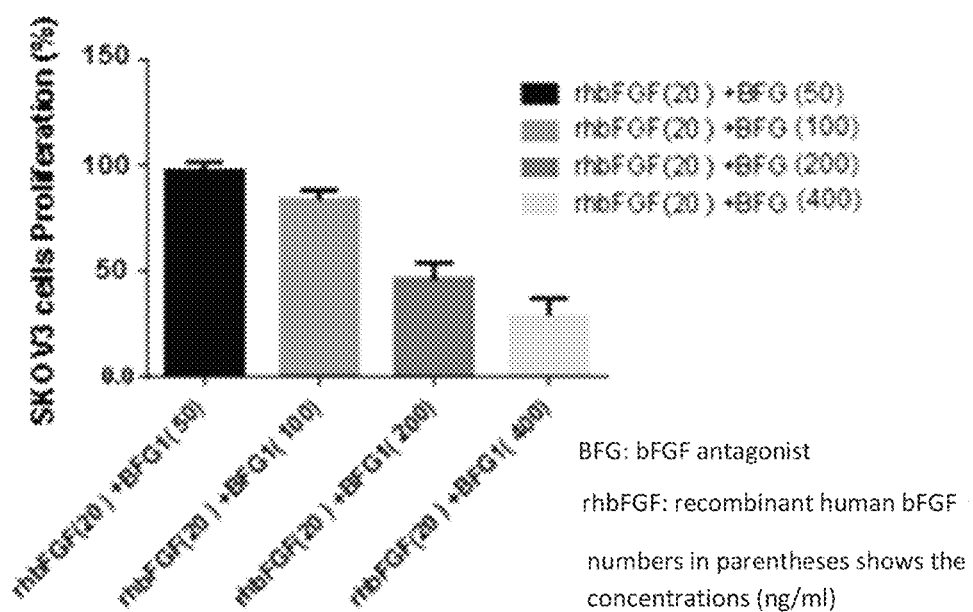
FIG. 4B is a bar graph illustrating the results obtained from the ovarian cancer cell line SKOV3 proliferation assay in presence of basic fibroblast growth factor (bFGF) antagonist, according to one embodiment herein.

FIG. 4B is a bar graph illustrating the results obtained from the ovarian cancer cell line SKOV3 proliferation assay in presence of basic fibroblast growth factor (bFGF) antagonist, according to one embodiment herein. FIG. 4B illustrate that the bFGF antagonist peptide inhibits the bFGF-induced proliferation of ovarian cancer cell line SKOV3 in a dose-dependent manner. FIG. 4B illustrate that when the concentration of the bFGF antagonist peptide is 400 ng/ml, then the cell proliferation is reduced.

Figure 5A:
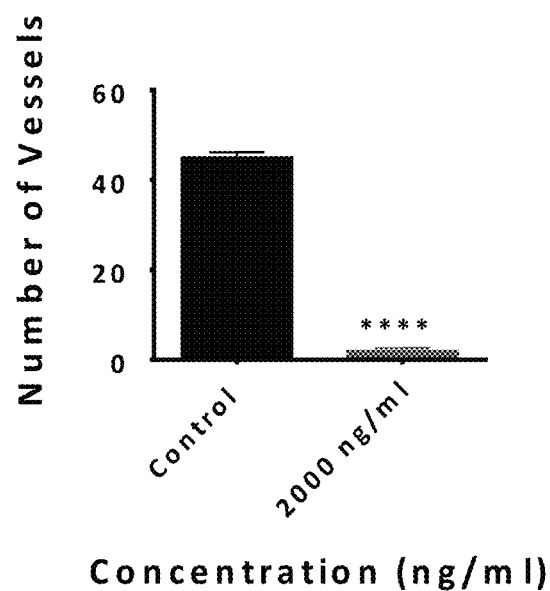
FIG. 5A is a bar graph illustrating the result obtained from the Matrigel assay conducted to analyze the anti-angiogenic activity of the vascular endothelial growth factor (VEGF) antagonist VEGF-1, according to one embodiment herein.

FIG. 5A is a bar graph illustrating the result obtained from the Matrigel assay conducted to analyze the anti-angiogenic activity of the vascular endothelial growth factor (VEGF) antagonist VEGF-1, according to one embodiment herein.

FIG. 5A illustrates that at a concentration of 2000 ng/ml vascular endothelial growth factor (VEGF) antagonist VEGF-1 inhibits the angiogenesis process.

Figure 5B:
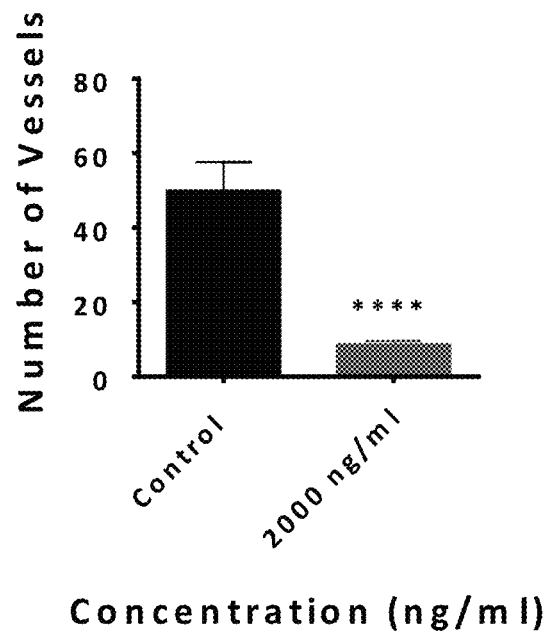
FIG. 5B is a bar graph illustrating the result obtained from the Matrigel assay conducted to analyze the anti-angiogenic activity of the basic fibroblast growth factor (bFGF) peptide, according to one embodiment herein.

FIG. 5B is a bar graph illustrating the result obtained from the Matrigel assay conducted to analyze the anti-angiogenic activity of the basic fibroblast growth factor (bFGF) peptide, according to one embodiment herein. FIG. 5B illustrates that at a concentration of 2000 ng/ml the basic fibroblast growth factor (bFGF) peptide inhibits the angiogenesis process.

Figure 6:
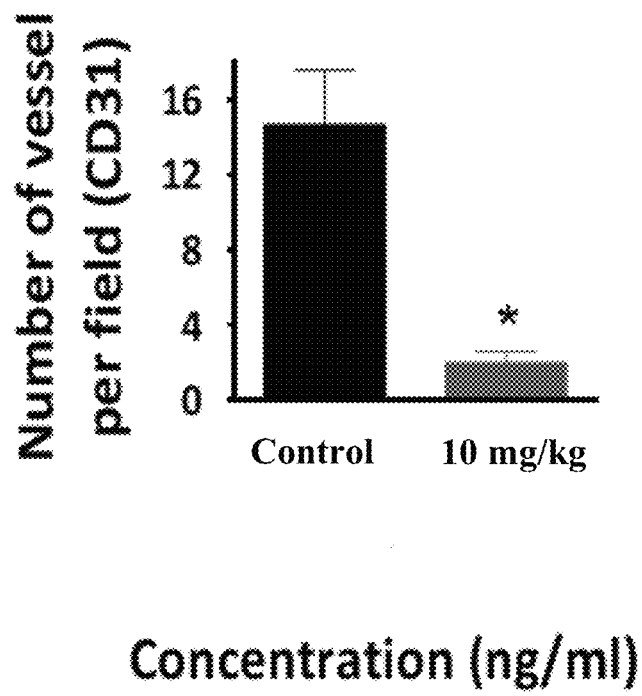
FIG. 6 is a bar graph illustrating anti-angiogenic effects of vascular endothelial growth factor (VEGF) peptide analyzed by histopathological staining of angiogenesis marker CD31, according to one embodiment herein. The bar graph illustrates that the VEGF peptide inhibits the angiogenesis.

FIG. 6 is a bar graph illustrating anti-angiogenic effects of vascular endothelial growth factor (VEGF) peptide analyzed by histopathological staining of angiogenesis marker CD31, according to one embodiment herein. The bar graph illustrates that the VEGF peptide inhibits the angiogenesis.

Figure 7:
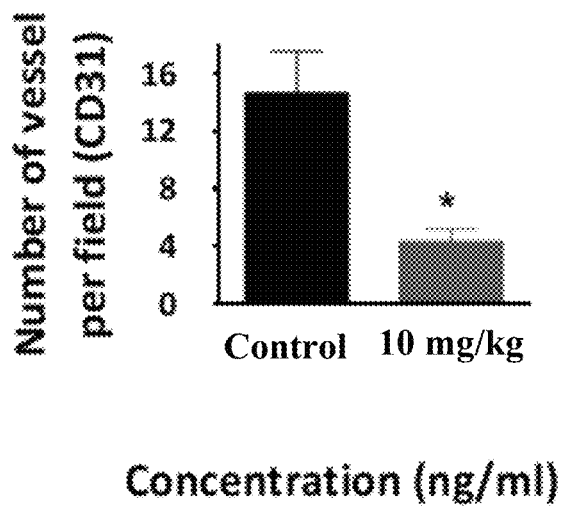
FIG. 7 is a bar graph illustrating anti-angiogenic effects of basic fibroblast growth factor (bFGF) peptide analyzed by histopathological staining of angiogenesis marker CD31, according to one embodiment herein. The photographs illustrate that the bFGF peptide inhibits the angiogenesis.

FIG. 7 is a bar graph illustrating anti-angiogenic effects of basic fibroblast growth factor (bFGF) peptide analyzed by histopathological staining of angiogenesis marker CD31, according to one embodiment herein. The photographs illustrate that the bFGF peptide inhibits the angiogenesis.

Figure 8:
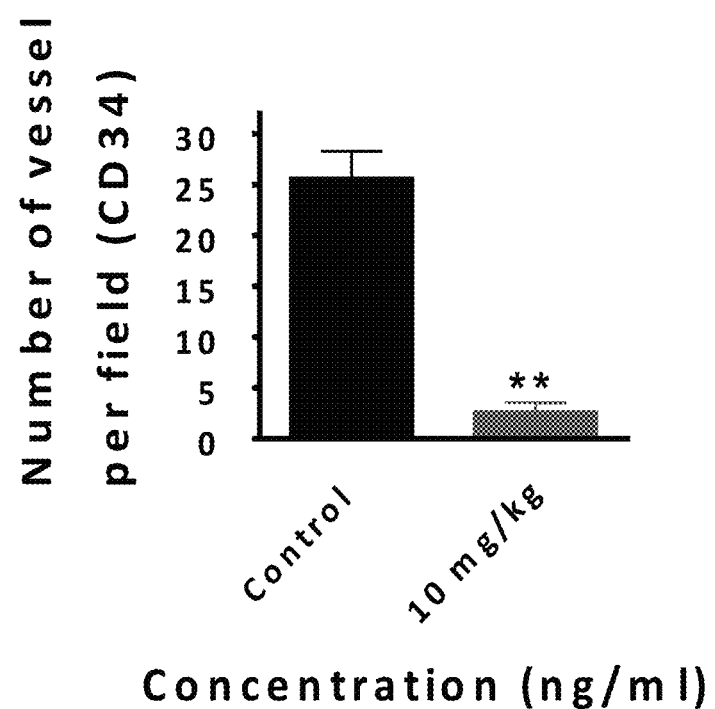
FIG. 8 is a bar graph illustrating anti-angiogenic effects of vascular endothelial growth factor (VEGF) peptide analyzed by histopathological staining of angiogenesis marker CD34, according to one embodiment herein. The bar graph illustrates that the VEGF peptide inhibits the angiogenesis.

FIG. 8 is a bar graph illustrating anti-angiogenic effects of vascular endothelial growth factor (VEGF) peptide analyzed by histopathological staining of angiogenesis marker CD34, according to one embodiment herein. The bar graph illustrates that the VEGF peptide inhibits the angiogenesis.

Figure 9:
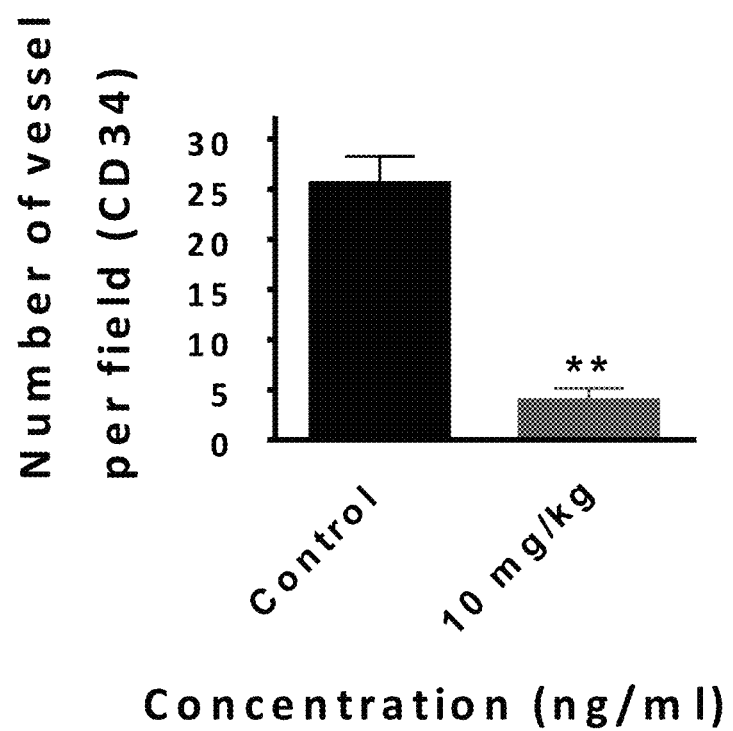
FIG. 9 is a bar graph illustrating anti-angiogenic effects of basic fibroblast growth factor (bFGF) peptide analyzed by histopathological staining of angiogenesis marker CD34, according to one embodiment herein. The bar graph illustrates that the bFGF peptide inhibits the angiogenesis.

FIG. 9 is a bar graph illustrating anti-angiogenic effects of basic fibroblast growth factor (bFGF) peptide analyzed by histopathological staining of angiogenesis marker CD34, according to one embodiment herein. The bar graph illustrates that the bFGF peptide inhibits the angiogenesis.

Figure 10A:
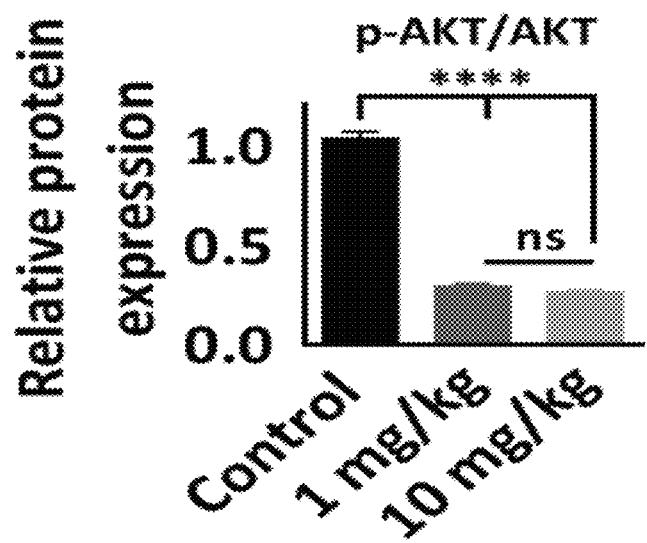
FIG. 10A and FIG. 10B are bar graphs together illustrating the results obtained from quantitative Western Blot Analysis of activation of PI3K/AKT and MAPK/ERK1/2 pathways on extract of murine 4T1 breast tumors treated by a VEGF-1 antagonist compared to control mice treated by PBS, according to one embodiment herein.
Figure 10B:
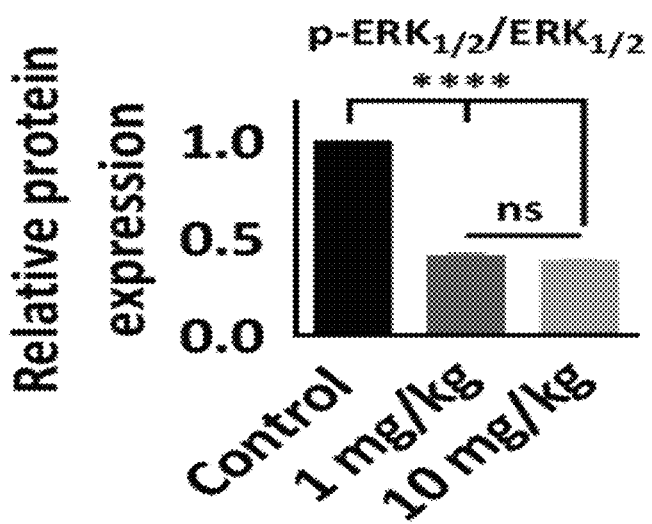

FIG. 10A and FIG. 10B are bar graphs together illustrating the results obtained from quantitative Western Blot Analysis of activation of PI3K/AKT and MAPK/ERK1/2 pathways on extract of murine 4T1 breast tumors treated by a VEGF-1 antagonist compared to control mice treated by PBS, according to one embodiment herein.

Figure 11A:
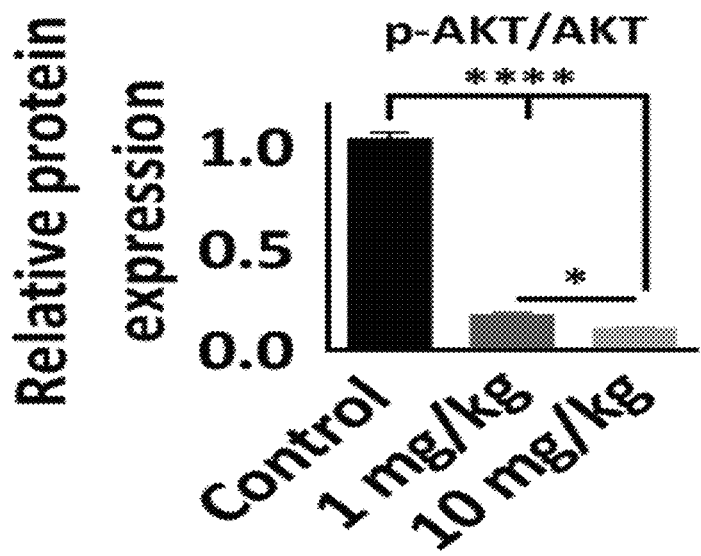
FIG. 11A and FIG. 11B are bar graphs together illustrating the results obtained from quantitative Western Blot analysis of the activation of PI3K/AKT and MAPK/ERK1/2 pathways on extract of murine 4T1 breast tumors treated by a bFGF antagonist compared to control mice treated by PBS, according to one embodiment herein.

FIG. 11A and FIG. 11A are bar graphs together illustrating the results obtained from quantitative Western Blot analysis of the activation of PI3K/AKT and MAPK/ERK1/2 pathways on extract of murine 4T1 breast tumors treated by a bFGF antagonist compared to control mice treated by PBS, according to one embodiment herein.

In the illustrate control normal (CN) which is PBS treated healthy mouse, VEGF treated healthy mouse (N1), bFGF treated healthy mouse (N2), control mouse (CT) or phosphate buffer saline (PBS) treated tumoric mouse, VEGF treated tumoric mouse (T1) and bFGF treated tumoric mouse (T2).

According to one embodiment herein, all the peptides and the peptide variants are antagonists of VEGF-A and/or VEGF-B or bFGF which exhibiting antiangiogenic activity. As a result, these peptides can be used alone or in combination for treating disorders associated with neovascularization or angiogenesis. The ability of peptide variants to regress the growth of breast tumor in mice confirms anti-neovascularization or anti-angiogenesis activity of these peptides.

According to one embodiment herein, the results illustrate that vascular endothelial growth factor (VEGF) antagonistic peptides are able to bind VEFGR-1 receptor and VEGFR-2 receptor. After VEGF antagonistic peptide binds to the receptor the VEGF antagonistic peptide suppress the proliferation of HUVECs, which highly expresses the VEGFR-1 and VEGFR-2 on its cell surface. Similarly, bFGF antagonistic peptide recognizes and binds bFGFR-1. In addition, this peptide could inhibit the proliferation of ovarian cell line SKOV3, which is found to highly express bFGFR-1 on its cell surface. These results mean that VEGF-A-induced proliferation of endothelial cells as well as bFGF-induced proliferation of SKOV3 cells was inhibited by VEGF and bFGF antagonists, respectively, through blockade of the respective receptors on the cell surface.

Figure 11B:
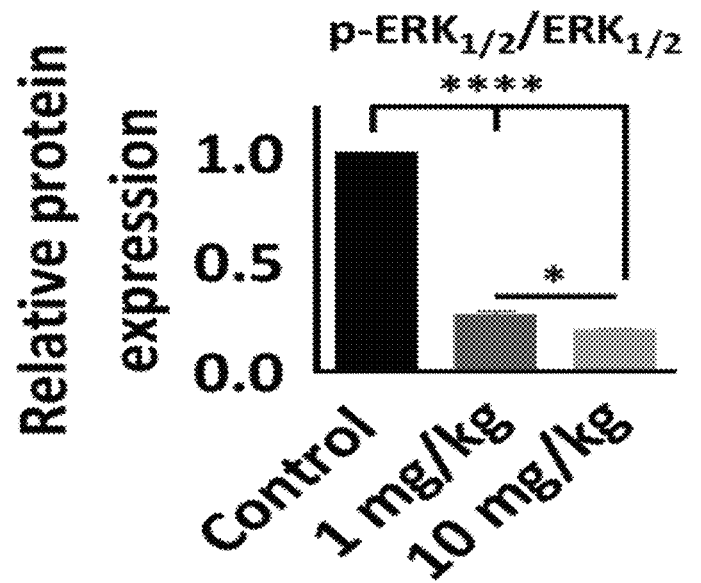

According to one embodiment herein, the results illustrate that vascular endothelial growth factor (VEGF) antagonist peptide (as illustrated in FIGS. 11A and 11B) and bFGF antagonist peptide (as illustrated in FIGS. 12A and 12B) are able to block AKT and ERK1/2 phosphorylation in 4T1 mammary carcinoma tumor tissues. Further the treatment with VEGF antagonist (1 and 10 mg/kg/day) is found to inhibit p-AKT and p-ERK1/2 levels in 4T1 mammary carcinoma tumor tissues on day 14 after administration. The inhibition is attributed to the effects of VEGF antagonist in tumor cells, as most of the cellular mass of the tumor comprises p-AKT and p-ERK1/2 pathways for cellular survival. Notably, there is no significant difference in both p-AKT or p-ERK inhibition levels with dosages of the bFGF antagonist peptide and VEGF antagonist peptide in a range of 1 and 10 mg/kg respectively.

According to one embodiment herein, angiogenesis-related disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with an anti-angiogenic effect, seem to prevent Alzheimer's disease and/or influence the outcome of AD patients. Therefore, it has been speculated that in AD angiogenesis in the brain vasculature may play an important role in AD. In Alzheimer's disease, the brain endothelium secretes the precursor substrate for the beta-amyloid plaque and a neurotoxic peptide that selectively kills cortical neurons. Moreover, amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies based on VEGF inhibition can interfere with endothelial cell activation in AD and can be used for preventing and/or treating AD.

According to one embodiment herein, the angiogenesis-related disease or disorder is obesity. It has been shown that the angiogenesis inhibitor, TNP-470 was able to prevent diet-induced and genetic obesity in mice. TNP-470 reduced vascularity in the adipose tissue, thereby inhibiting the rate of growth of the adipose tissue and obesity development. Thus, inhibition of angiogenesis can be therapeutic for obesity.

According to one embodiment herein, the angiogenesis-related disease or disorder is endometriosis. Excessive endometrial angiogenesis is proposed as an important mechanism in the pathogenesis of endometriosis. The endometrium of patients with endometriosis shows enhanced endothelial cell proliferation. Moreover, there is an elevated expression of the cell adhesion molecule integrin v133 in more blood vessels in the endometrium of women with endometriosis when compared with normal women. Strategies that inhibit angiogenesis can be used to treat endometriosis.

According to one embodiment herein, a pharmaceutical composition comprising a FGF- or VEGF-R binding peptide and a pharmaceutically acceptable carrier can be made. In another embodiment, the invention provides for a pharmaceutical composition comprising an expression vector carrying a peptide DNA sequence that encodes the FGF- or VEGF-R binding peptide and a pharmaceutically acceptable carrier. In yet another embodiment, the invention provides for a pharmaceutical composition comprising the host viral cells (vectors) harboring the DNA sequence that encodes the FGF- or VEGF-R binding peptide and a pharmaceutically acceptable carrier.

According to one embodiment herein, the term "pharmaceutical composition" refers to the active agent in combination with a pharmaceutically acceptable carrier of chemicals and compounds commonly used in the pharmaceutical industry. The term "pharmaceutically acceptable carries" excludes tissue culture medium.

According to one embodiment herein, for angiogenic diseases or disorders that are accessible externally on the skin, such as dermal hemangiomas and skin cancer lesions (melanoma), gene therapy virus, expression vectors, or the FGF- or VEGF-R binding peptide can be preferably applied topically to the hemangioma or cancer lesion site in a therapeutically effective amount in admixture with pharmaceutical carriers, in the form of topical pharmaceutical compositions. The gene therapy virus can be in the form of an adenovirus, adeno-associated virus or lentivirus. Such compositions include solutions, suspensions, lotions, gels, creams, ointments, emulsions, skin patches, etc. All of these dosage forms, along with methods for their preparation, are well known in the pharmaceutical and cosmetic art. Typically, such topical formulations contain the active ingredient in a concentration range of 0.1 to 100 mg/ml, in admixture with suitable vehicles. A suitable vehicle will not promote an immune response to the peptides described herein. For gene therapy viruses, the dosage ranges from 10(6) to 10(14) particles per application. Other desirable ingredients for use in such preparations include preservatives, co-solvents, viscosity building agents, carriers, etc. The carrier itself or a component dissolved in the carrier may have palliative or therapeutic properties of its own, including moisturizing, cleansing, or anti-inflammatory/anti-itching properties. Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

According to one embodiment herein, topical administration of a pharmacologically effective amount may utilize transdermal delivery systems well known in the art. An example is a dermal patch. Alternatively, the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The FGF- or VEGF-R binding peptide, expression vector, and/or gene therapy virus can be coated on minute gold particles, and these coated particles are "shot" into biological tissues such as hemangiomas and melanoma under high pressure.

According to one embodiment herein, the VEGF and bFGF antagonistic peptide compositions described herein can be administered directly by injection. If the solid tumors and hemangiomas are accessible by injection, the FGF- or VEGF-R binding peptide, expression vector, and/or viral vector can be administered by injection directly to the tumor mass as a pharmaceutical formulation. The preferred formulation is also sterile saline or Lactated Ringer's solution. Lactated Ringer's solution is a solution that is isotonic with blood and intended for intravenous administration.

In the treatment and prevention of diabetic retinopathy and wet macular degeneration, the present invention can be applied to the eye by injection as a pharmaceutical formulation. The injection directly introduces the FGF- or VEGF-R binding peptide into the vitreous humor. In one embodiment, the invention compositions can be formulated as an eye drop solution for direct application on the eyes.

According to one embodiment herein, in addition to topical therapy, the VEGF and bFGF antagonistic peptide compositions herein can also be administered systemically in a pharmaceutical formulation. Systemic routes include but are limited to oral, parenteral, nasal inhalation, intratracheal, intrathecal, intracranial, and intrarectal. The pharmaceutical formulation is preferably a sterile saline or lactated Ringer's solution. For therapeutic applications, the preparations described herein are administered to a mammal, preferably a human, in a pharmaceutically acceptable dosage form, including those that may be administered to a human intravenously as a bolus or by continuous infusion over a period of time, by intramuscular, intraperitoneal, intracerebrospinal, subcutaneous, intra-arterial, intrasynovial, intrathecal, oral, topical, or inhalation routes. A preferred embodiment is the intramuscular injection of AAV viral vectors encoding a FGF- or VEGF-R binding peptide and/or its variant forms. The compositions described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required. In one embodiment, the therapeutic compositions described herein are formulated in a cationic liposome formulation such as those described for intratracheal gene therapy treatment of early lung cancer. The liposome formulations are especially suitable for aerosol use in lung cancer patients. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethylene glycol (PEG) coating. Other techniques in formulating expression vectors and virus as therapeutics are previously described. In one embodiment, the dosage for viral vectors is 10(6) to 1×10 (14) viral vector particles per application per patient.

According to one embodiment herein, the route of administration, dosage form, and the effective amount vary according to the potency of the FGF- or VEGF-R binding peptide, expression vectors and viral vectors, their physicochemical characteristics, and according to the treatment location. The selection of proper dosage is well within the skill of an ordinarily skilled physician. Topical formulations can be administered up to four-times a day.

According to one embodiment herein, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of peptide include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. The peptide will usually be formulated in such vehicles at a concentration of about 0.1 mg/ml to 100 mg/ml and the viral vector should be in the range of 10(6) to 1×10(14) viral vector particles per application per patient.

According to one embodiment herein, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

According to one embodiment herein, the pharmaceutical formulation to be used for therapeutic administration must be sterile. Sterility is readily accomplished by filtration through sterile filtration membranes (e.g., 0.2 micron membranes). The FGF- or VEGF-R binding peptide ordinarily will be stored in lyophilized form or as an aqueous solution if it is highly stable to thermal and oxidative denaturation. The pH of the FGF- or VEGF-R binding peptide preparations typically will be about from 6 to 8, although higher or lower pH values may also be appropriate in certain instances.

According to one embodiment herein, for the prevention or treatment of angiogenic disease or disorder, the appropriate dosage of bFGF- or VEGF-R binding peptide and/or viral vectors will depend upon the type of disease or disorder to be treated, the severity and course of the disease, whether the bFGF-R or VEGF-R binding peptide are administered for preventative or therapeutic purposes, previous therapy, the patient's clinical history and response to the FGF- or VEGF-R binding peptide and/or viral vectors and the discretion of the attending physician. The FGF- or VEGF-R binding peptide and/or viral vectors are suitably administered to the patient at one time or over a series of treatments. For purposes herein, the "therapeutically effective amount" of a FGF- or VEGF-R binding peptide or viral vector is an amount that is effective to either prevent, lessen the worsening of, alleviate, or cure the treated condition, in particular that amount which is sufficient to reduce or inhibit the proliferation of vascular endothelium in vivo.

It is to be understood that the phraseology or terminology employed herein is for description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method for synthesizing antagonistic peptides for vascular endothelial growth factor (VEGF) and basic fibroblast growth factor (bFGF), the method comprises the steps of:
synthesizing the antagonistic peptides for vascular endothelial growth factor (VEGF) and basic fibroblast growth factor (bFGF) by a protocol;
analyzing a purity of the antagonistic peptides for vascular endothelial growth factor (VEGF) and basic fibroblast growth factor (bFGF) by a protocol; and
analyzing a plurality of physic-chemical qualities of the antagonistic peptides for vascular endothelial growth factor (VEGF) and basic fibroblast growth factor (bFGF) by a plurality of methods, and wherein the plurality of methods are HPLC chromatogram and Mass spectrometry analysis, and wherein cyclization in the antagonistic peptides for vascular endothelial growth factor (VEGF) and basic fibroblast growth factor (bFGF) is analyzed by a protocol, and wherein the synthesized antagonistic peptides for vascular endothelial growth factor (VEGF) and basic fibroblast growth factor (bFGF) are annotated as Seq. ID No. 1 peptide, Seq. ID No. 2 peptide, Seq. ID No. 3 peptide, Seq. ID No. 4 peptide and Seq. ID No. 5 peptide, and wherein the Seq. ID No. 1 peptide, Seq. ID No. 2 peptide, Seq. ID No. 3 peptides are antagonists of both VEGF-A and VEGF-B, and wherein the Seq. ID No. 1 peptide, Seq. ID No. 2 peptide, Seq. ID No. 3 peptides in combination act as antagonists for both VEGF-A and VEGF-B, and wherein the Seq. ID No. 4 peptide is an antagonist of VEGF-A, and wherein the Seq. ID No. 5 peptide is an antagonist of bFGF, and wherein the biochemical activity of the antagonistic peptides for vascular endothelial growth factor (VEGF) and basic fibroblast growth factor (bFGF) is analyzed by competitive binding assay, cell proliferation assay, Matrigel assay for anti-angiogenic activity analysis, histopathological staining and Western blot analysis.

2. The method according to claim 1, wherein the Seq. ID No. 1 peptide comprises a biochemical structure represented by H2N-Cys-Gln-Val-Leu-Ile-Ser-Gln-Leu-Cys-COOH, and wherein the Seq. ID No. 1 comprises seven amino acid residues derived from VEGF-B (Gln46, Val48, Leu81, Ile83, Ser88, Gln89 and Leu90), and wherein the Seq. ID No. 1 comprises two Cys residues for chain cyclization, and wherein the Seq. ID No. 1 peptide binds and blocks vascular endothelial growth factor receptor-1 and vascular endothelial growth factor receptor-2 (VEGFR-1 and VEGFR-2).

3. The method according to claim 1, wherein the Seq. ID No. 2 peptide comprises amino acid residues derived from VEGF-B, and wherein the Seq. ID No. 2 comprises amino acid residues 61-70 in VEGF-B, and wherein the Seq. ID No. 2 comprises a biochemical structure represented by H2N-Cys$^{61}$-Pro$^{62}$-Asp$^{63}$-Asp$^{64}$-Gly$^{65}$-Leu$^{66}$-Glu$^{67}$-Cys$^{68}$-Val$^{69}$-Pro$^{70}$-COOH, and wherein the Seq. ID No. 2 peptide binds and blocks vascular endothelial growth factor receptor-1 and vascular endothelial growth factor receptor-2 (VEGFR-1 and VEGFR-2).

4. The method according to claim 1, wherein the Seq. ID No. 3 peptide comprises amino acid residues derived from VEGF-B, and wherein the Seq. ID No. 3 comprises amino acid residues 101-105 in VEGF-B, and wherein the Seq. ID No. 3 comprises a biochemical structure represented by H$_2$N-Cys$^{101}$-Glu$^{102}$-Cys$^{103}$-Arg$^{104}$-Pro$^{105}$-COOH, and wherein the Seq. ID No. 3 peptide binds and blocks vascular endothelial growth factor receptor-1 and vascular endothelial growth factor receptor-2 (VEGFR-1 and VEGFR-2).

5. The method according to claim 1, wherein the Seq. ID No. 4 peptide comprises amino acid residues derived from VEGF-A, and wherein Seq. ID No. 4 comprises amino acid residues 34-51 in VEGF-A, and wherein the Seq. ID No. 4 comprises a biochemical structure represented by H2N-Asp$^{34}$-Ile$^{35}$-Phe$^{36}$-Gln$^{37}$-Glu$^{38}$-Tyr$^{39}$-Pro$^{40}$-Asp$^{41}$-Glu$^{42}$-Ile$^{43}$-Glu$^{44}$-Tyr$^{45}$-Ile$^{46}$-Phe$^{47}$-Lys$^{48}$-Pro$^{49}$-Ser$^{50}$-Cys$^{51}$-COOH, and wherein a cysteine residue is added optionally to the N-terminus of Seq. ID No. 4 for chain cyclization, and wherein the Seq. ID No. 4 peptide binds and blocks vascular endothelial growth factor receptor 2 (VEGFR-2).

6. The method according to claim 1, wherein Seq. ID No. 1 peptide, Seq. ID No. 2 peptide, Seq. ID No. 3 peptide and Seq. ID No. 4 peptide bind and block vascular endothelial growth factor receptors 1 (VEGFR-1) and/or vascular endothelial growth factor receptors 2 (VEGFR-2), and wherein a combination of Seq. ID No. 1 peptide, Seq. ID No. 2 peptide, Seq. ID No. 3 peptide and Seq. ID No. 4 peptide bind and block vascular endothelial growth factor receptors 1 (VEGFR-1) and/or vascular endothelial growth factor receptors 2 (VEGFR-2).

7. The method according to claim 1, wherein the Seq. ID No. 5 peptide comprises amino acid residues derived from bFGF, and wherein the Seq. ID No. 5 comprises a biochemical structure represented by H$_2$N-Leu$^{119}$-Lys$^{120}$-Arg$^{121}$-Thr$^{122}$-Gly$^{123}$-Gln$^{124}$-Tyr$^{125}$-Lys$^{126}$-Leu$^{127}$-COOH, and wherein cysteine residues are added to the N-terminus and C-terminus of Seq. ID No. 5 to obtain a Seq. ID No. 6 having a biochemical structure represented by H2N-Cys-Leu-Lys-Arg-Thr-Gly-Gln-Tyr-Lys-Leu-Cys-COOH, and wherein the Seq. ID No. 6 peptide binds and blocks vascular endothelial growth factor receptor 1 (VEGFR-1) and/or vascular endothelial growth factor receptor 2 (VEGFR-2) and basic fibroblast growth factor-receptor 1 (bFGFR-1) with a combination of Seq. ID No. 5 peptide and at least one of Seq. ID No. 1 to Seq. ID No. 4.

8. The method according to claim 1, wherein a plurality of diagnostic, therapeutic and theranostic properties of Seq. ID No. 1-Seq. ID No. 5 antagonistic peptides are observed against VEGF and bFGF, and wherein the diagnostic, therapeutic and theranostic properties of Seq. ID No. 1-Seq. ID No. 5 peptides are observed in VEGF and bFGF antagonistic sequences along with a pharmaceutically acceptable carrier, and wherein the Seq. ID No. 1-Seq. ID No. 5 peptides are linked to a heterologous peptide and/or protein, and wherein the theranostic property is also used in topically administering a plurality of therapeutic compositions, and wherein the plurality of therapeutic compositions are selected from the group consisting of cream, lotion, solution and lip balm.

9. The method according to claim 1, wherein the Seq. ID No. 1-Seq. ID No. 5 peptides exhibit anti-angiogenesis activity, and wherein the Seq. ID No. 1-Seq. ID No. 5 peptides are useful for treatment of an angiogenesis-related disease, and wherein the angiogenesis-related disease are selected from the group consisting of cancer, ascites formation, psoriasis, age-related macular degeneration, thyroid hyperplasia, preeclampsia, rheumatoid arthritis, osteoarthritis, Alzheimer's disease, obesity, pleura effusion, atherosclerosis, endometriosis, diabetic/other retinopathies, neovascular glaucoma, age-related macular degeneration, hemangiomas, and corneal neovascularization.

10. The method according to claim 1, wherein the competitive binding assay of antagonistic peptide for vascular endothelial growth factor (VEGF) and basic fibroblast growth factor (bFGF) is configured to bind with a plurality of cell receptors at a concentration of 2000 ng/ml, and wherein the cell proliferation assay illustrates that the cell growth is arrested when the antagonistic peptide for vascular endothelial growth factor (VEGF) and basic fibroblast growth factor (bFGF) are present at a concentration of 2000 ng/ml, and wherein the anti-angiogenic activity result analysis illustrates that the angiogenesis in the cells is arrested when the concentration of antagonistic peptide for vascular endothelial growth factor (VEGF) and basic fibroblast growth factor (bFGF) is 2000 ng/ml.

* * * * *